United States Patent
Benkler et al.

(10) Patent No.: US 10,220,077 B2
(45) Date of Patent: Mar. 5, 2019

(54) COMBINATION TREATMENT FOR AMYOTROPHIC LATERAL SCLEROSIS (ALS)

(71) Applicant: Daniel Offen, Kfar HaRoe (IL)

(72) Inventors: Chen Benkler, Tel-Aviv (IL); Daniel Offen, Kfar HaRoe (IL)

(73) Assignee: RAMOT AT TEL-AVIV UNIVERSITY LTD., Tel-Aviv (IL)

(*) Notice: Subject to any disclaimer, the term of this patent is extended or adjusted under 35 U.S.C. 154(b) by 0 days.

(21) Appl. No.: 14/442,731

(22) PCT Filed: Nov. 14, 2013

(86) PCT No.: PCT/IL2013/050943
§ 371 (c)(1),
(2) Date: May 14, 2015

(87) PCT Pub. No.: WO2014/076702
PCT Pub. Date: May 22, 2014

(65) Prior Publication Data
US 2015/0290298 A1  Oct. 15, 2015

Related U.S. Application Data

(60) Provisional application No. 61/726,050, filed on Nov. 14, 2012.

(51) Int. Cl.
| | | |
|---|---|---|
| *A61K 38/17* | (2006.01) | |
| *A61K 38/44* | (2006.01) | |
| *A61K 45/06* | (2006.01) | |
| *A61K 48/00* | (2006.01) | |
| *A61K 38/43* | (2006.01) | |

(52) U.S. Cl.
CPC .......... *A61K 38/44* (2013.01); *A61K 38/1709* (2013.01); *A61K 38/43* (2013.01); *A61K 45/06* (2013.01); *A61K 48/005* (2013.01); *A01K 2227/105* (2013.01); *A01K 2267/0318* (2013.01); *A61K 48/00* (2013.01); *C12N 2740/15043* (2013.01); *C12Y 104/01003* (2013.01)

(58) Field of Classification Search
None
See application file for complete search history.

(56) References Cited

U.S. PATENT DOCUMENTS

| 2006/0024284 A1* | 2/2006 | Teichberg | A61K 31/19 424/94.5 |
| 2010/0166880 A1* | 7/2010 | Plaitakis | A61K 31/00 424/600 |

FOREIGN PATENT DOCUMENTS

| WO | WO 2004071419 A2 * | 8/2004 | .......... A61K 31/352 |
| WO | WO 2007005879 A2 * | 1/2007 | .......... A01K 67/027 |

OTHER PUBLICATIONS

Chang et al. "Protective effect of combination of sulforaphane and riluzole on glutamate-mediated excitotoxicity", Biology Pharmaceutical Bulletin 33(9): 1477-1483, 2010.*
Lewerenz et al. "Induction of Nrf2 and xCT are involved in the action of the neuroprotective antibiotic ceftriaxone in vitro", Journal of Neurochemistry 111: 332-343, 2009.*
Burton et al; "In vivo modulation of the Parkinsonian phenotype by Nrf2" NeuroToxicology 27 pp. 1094-1100. (2006).
Calkins et al; "Astrocyte-Specific Overexpression of Nrf2 Protects Striatal Neurons from Mitochondrial Complex II Inhibition" Toxicological Sciences 115(2), pp. 557-568. (2010).
Glavas et al; "Active Site Residues of Glutamate Racemase" Biochemistry 40, pp. 6199-6204.(2001).
Glenn Lin et al; "Glutamate transporter EAAT2: a new target for the treatment of neurodegenerative diseases" Future Medicinal Chemistry 4(13): pp. 1689-1700. (2012).
Gomes; "Aspirin: a neuroprotective agent at high doses?" The National medical journal of India. 11(1):1pp. 4-7.(1998).
Kraft et al; "Nuclear Factor E2-Related Factor 2-Dependent Antioxidant Response Element Activation by tert-Butylhydroquinone and Sulforaphane Occurring Preferentially in Astrocytes Conditions Neurons against Oxidative Insult" The Journal of Neuroscience, 24(5):pp. 1101-1112. (2004).
Leonard et al; "Reoxygenation-specific activation of the antioxidant transcription factor Nrf2 mediates cytoprotective gene expression in ischemia-reperfusion injury" FASEB journal 20(14):pp. 2166-2176. (2006).
Rothstein et al; "Chronic inhibition of glutamate uptake produces a model of slow neurotoxicity" PNAS vol. 90, pp. 6591-6595. (1993).
Rothstein et al; "Beta-lactam antibiotics offer neuroprotection by increasing glutamate transporter expression" Nature. 6;433(7021):pp. 73-77. (2005).
Satoh et al; "Activation of the Keap1Nrf2 pathway for neuroprotection by electrophillic phase II inducers" PNAS vol. 103 No. 3. pp. 768-773. (2006).
Satoh et al; "Carnosic acid, a catechol-type electrophilic compound, protects neurons both in vitro and in vivo through activation of the Keap1/Nrf2 pathway via S-alkylation of targeted cysteines on Keap1" J Neurochem. 104(4): pp. 1116-1131. (2008).
Shih et al; "Coordinate Regulation of Glutathione Biosynthesis and Release by Nrf2-Expressing Glia Potently Protects Neurons from Oxidative Stress" The Journal of Neuroscience, 23(8):pp. 3394-3406. (2003).

(Continued)

*Primary Examiner* — Emily A Cordas
(74) *Attorney, Agent, or Firm* — Knobbe, Martens, Olson & Bear, LLP

(57) ABSTRACT

A method of treating a disease selected from the group consisting of emphysema, sepsis, septic shock, ischemic injury, cerebral ischemia, a neurodegenerative disorder, meningitis, encephalitis, hemorrhage, cerebral ischemia, heart ischemia and a cognitive deficit in a subject in need thereof is provided. The method comprising administering to the subject a therapeutically effective amount of a combination of at least two agents, wherein a first of said two agents upregulates an activity and/or expression of Nrf2 and a second of said two agents is a glutamatergic modulator, thereby treating the disease.

6 Claims, 23 Drawing Sheets
(1 of 23 Drawing Sheet(s) Filed in Color)

Specification includes a Sequence Listing.

(56) References Cited

OTHER PUBLICATIONS

Shih et al; "A Small-Molecule-Inducible Nrf2-Mediated Antioxidant Response Provides Effective Prophylaxis against cerebral Ischemia In Vivo" The Journal of Neuroscience, 25(44):pp. 10321-10335. (2005).
Shih et al; "Induction of the Nrf2-driven Antioxidant Response Confers Neuroprotection during Mitochondrial Stress in Vivo" The Journal of Biological Chemistry vol. 280, No. 24, pp. 22925-22936. (2005).
Stringer et al; "The effects of gabapentin in the rat hippocampus are mimicked by two structural analogs, but not by nimodipine" Epilepsy Research 41 pp. 15-162. (2000)/.
Vargas et al; "The Nrf2—ARE cytoprotective pathway in astrocytes" expert reviews vol. 11; e17. pp. 1-20. (2009).
Zhao et al; "Enhancing Expression of Nrf2-Driven Genes Protects the Blood-Brain Barrier after Brain Injury" The Journal of Neuroscience,27(38):pp. 10240-10248. (2007).
Zhao et al; "Transcription Factor Nrf2 Protects the Brain From Damage Produced by Intracerebral Hemorrhage" Stroke. 38(12):pp. 3280-3286. (2007).
Bryan et al; "The Nrf2 cell defence pathway: Keap1-dependent and -independent mechanisms of regulation" Biochemical Pharmacology 85 pp. 705-717. (2013).
Tate "Overexpression of mammalian integral membrane proteins for structural studies" FEBS Letters 504 (3):pp. 94-98. (2001).

\* cited by examiner

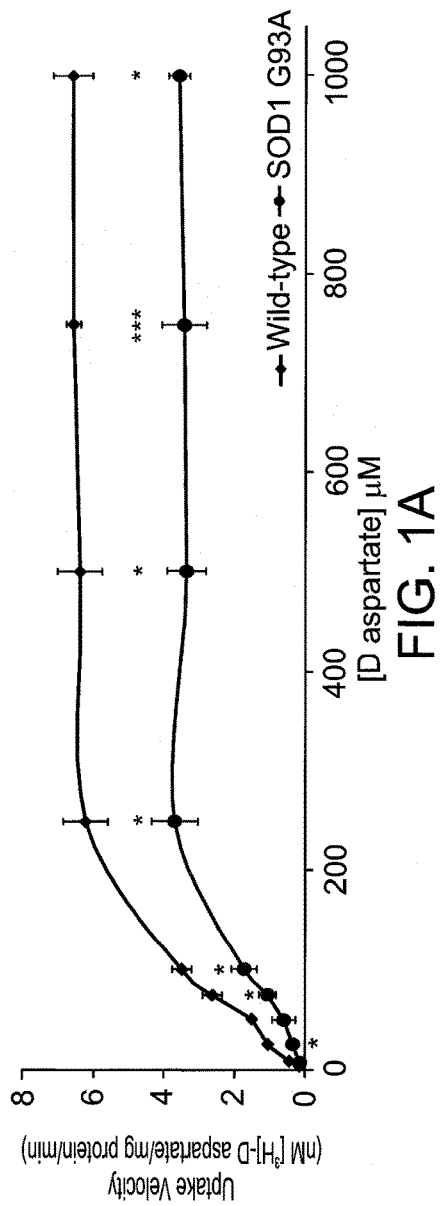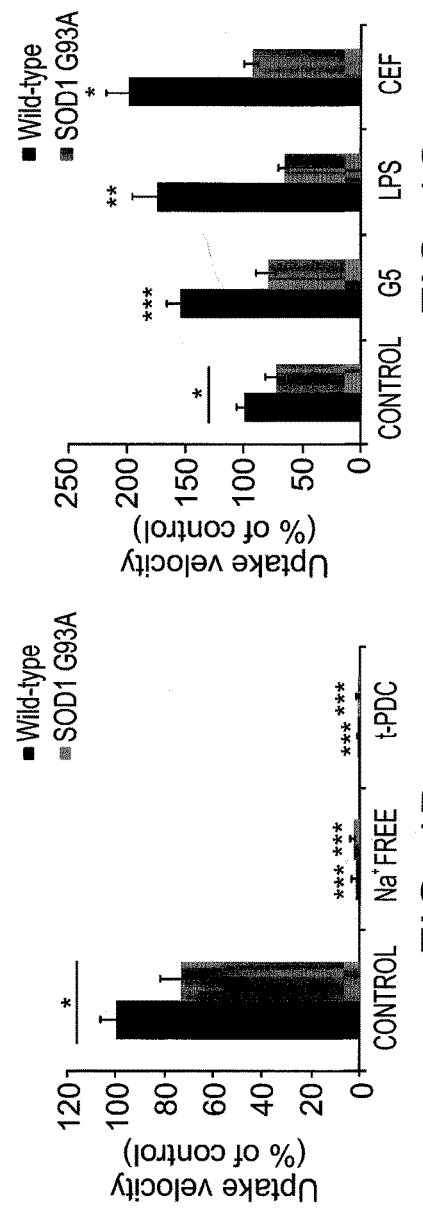

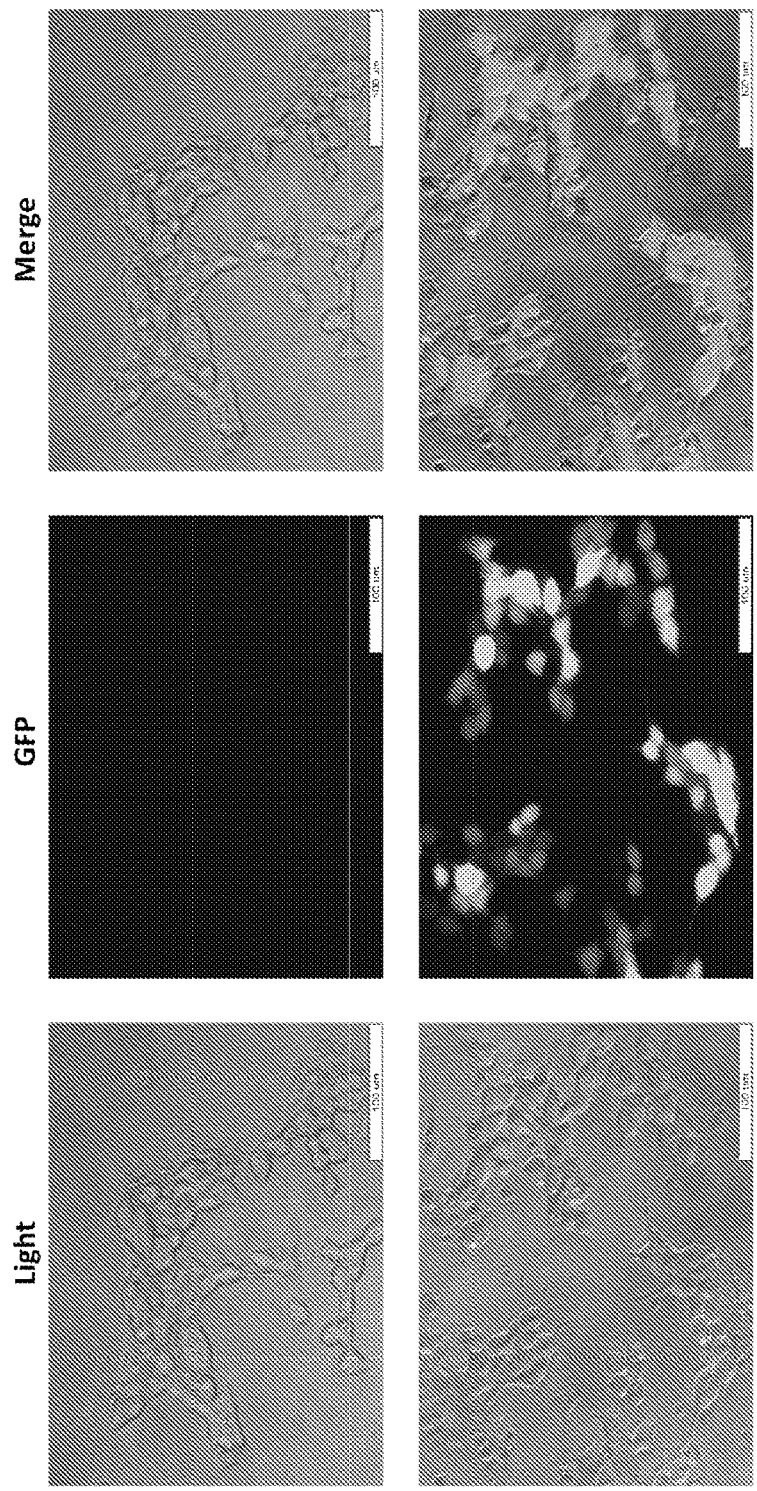

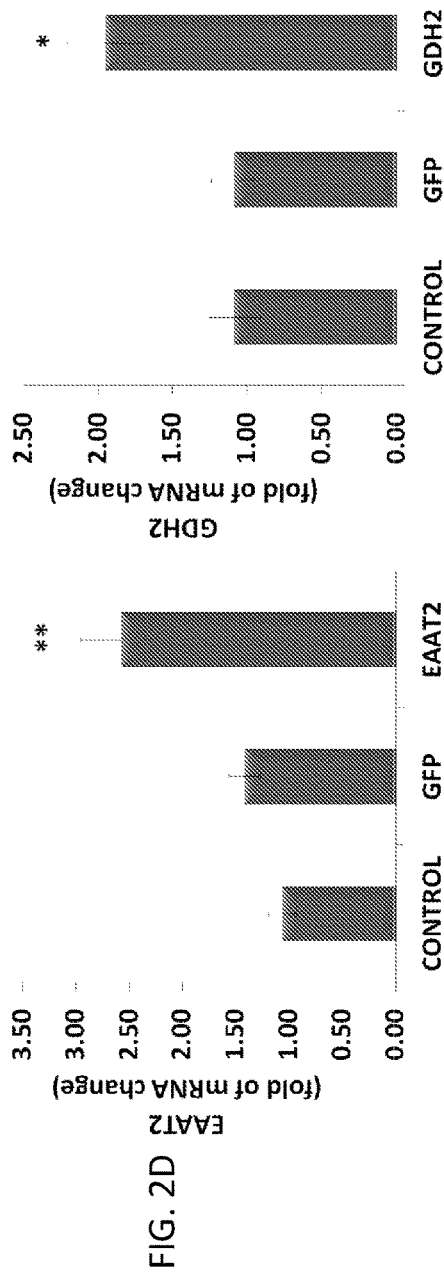
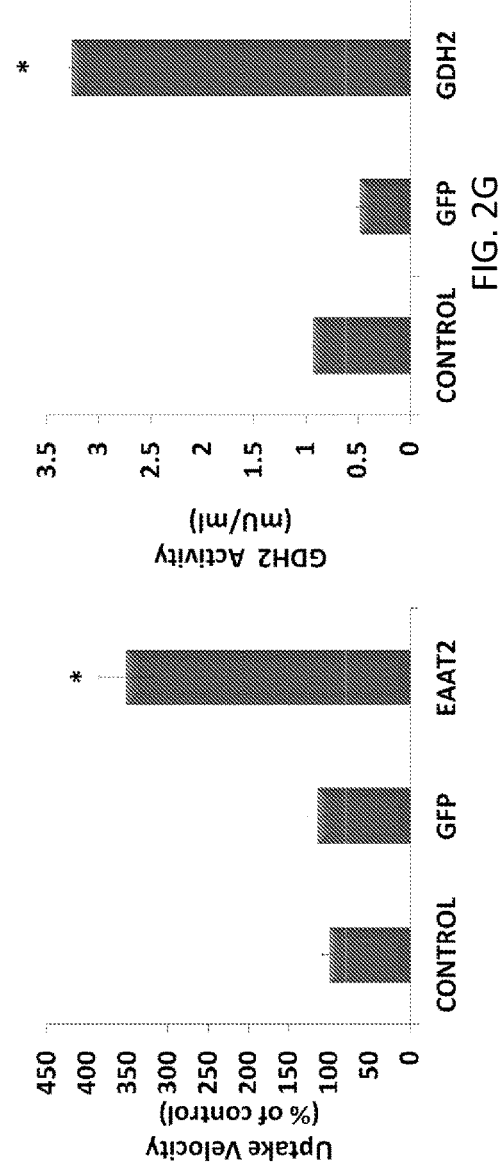

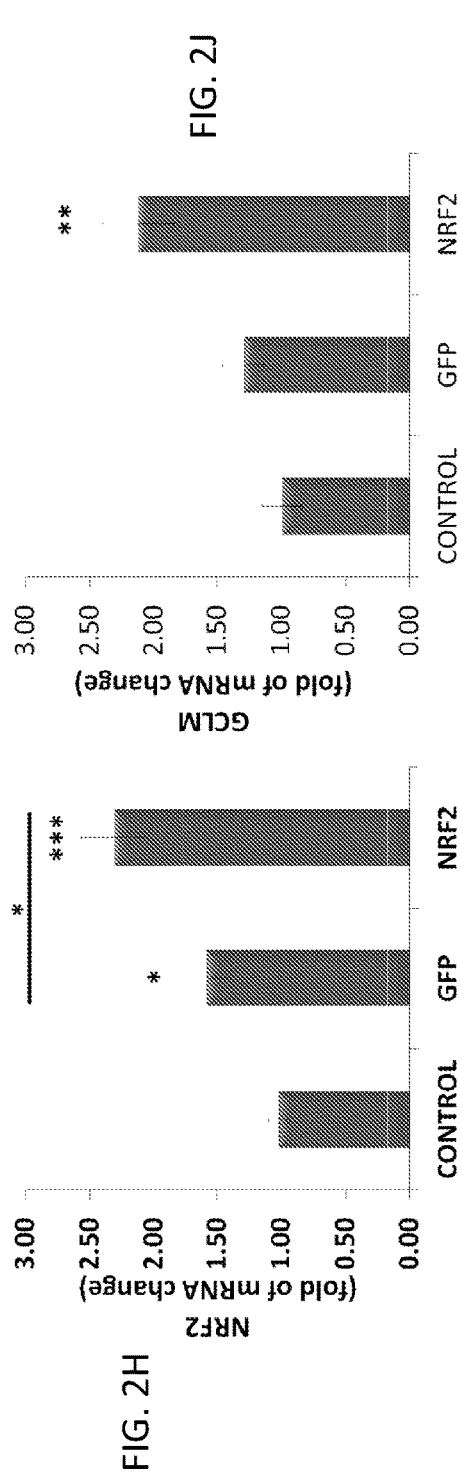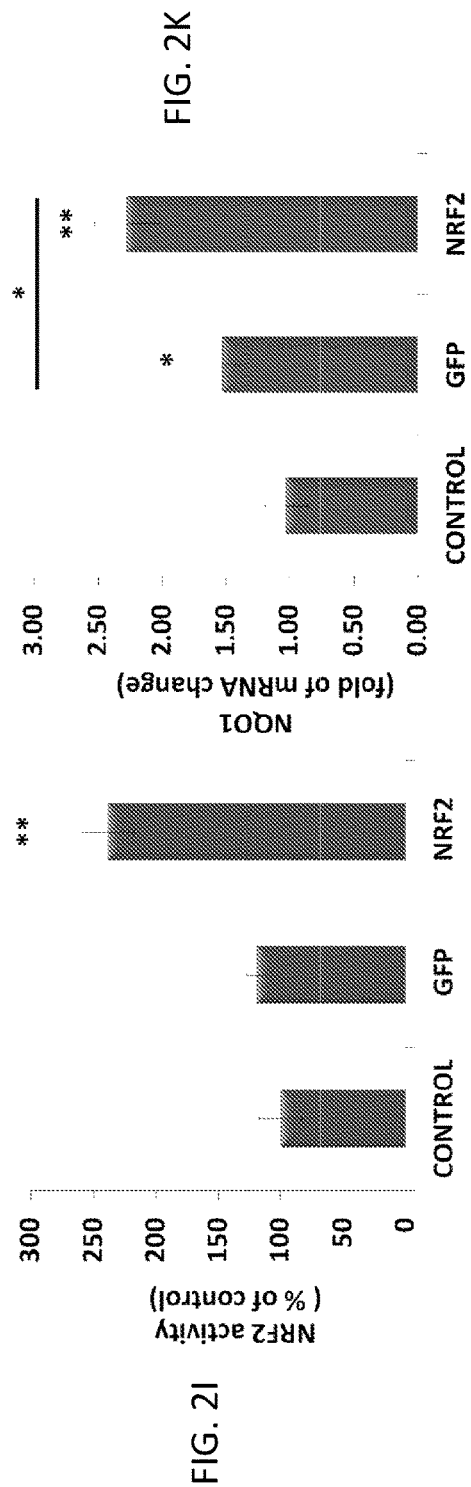

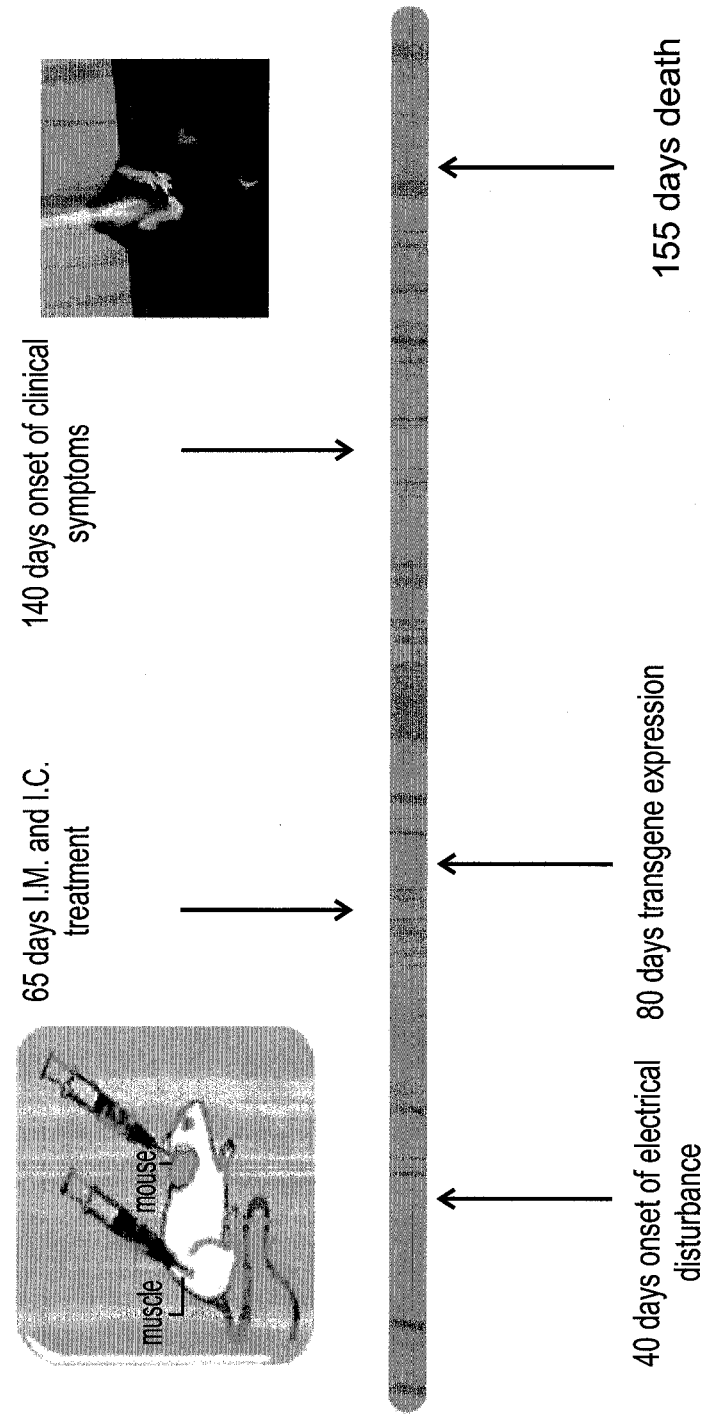

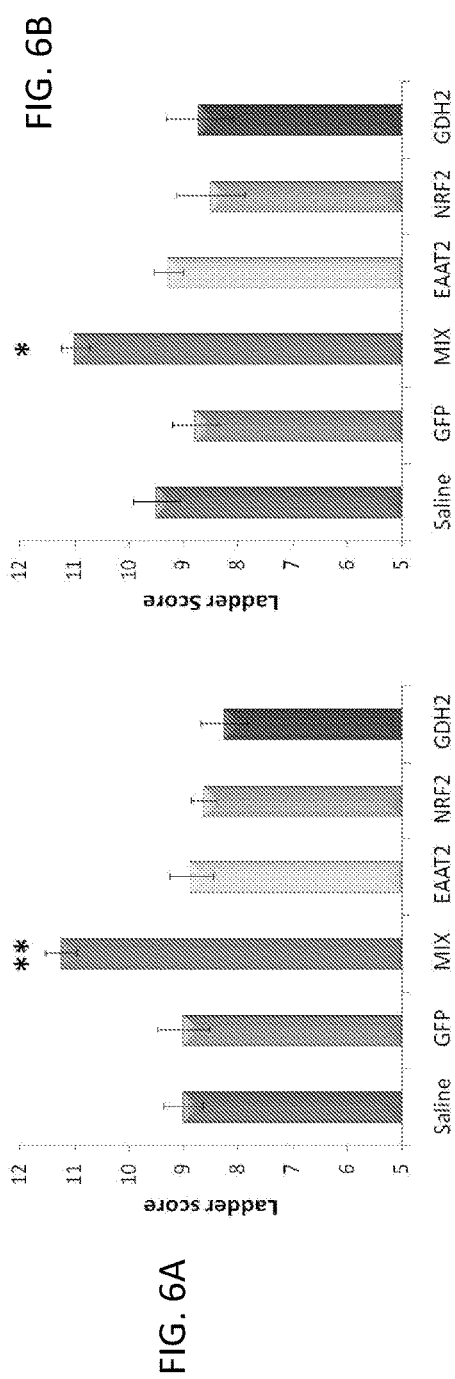
FIG. 6A
FIG. 6B
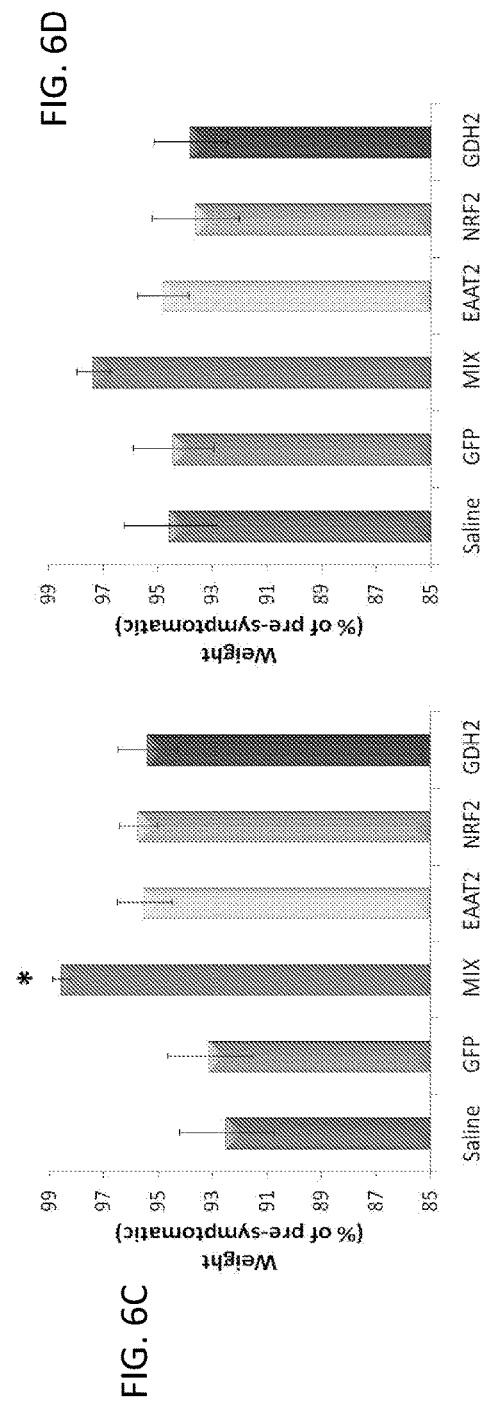
FIG. 6C
FIG. 6D

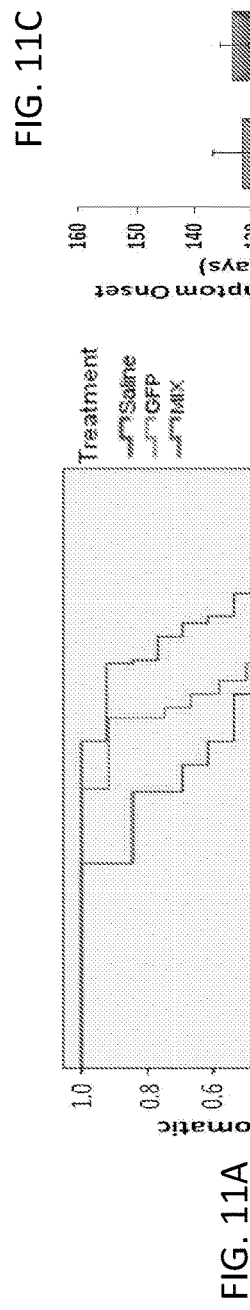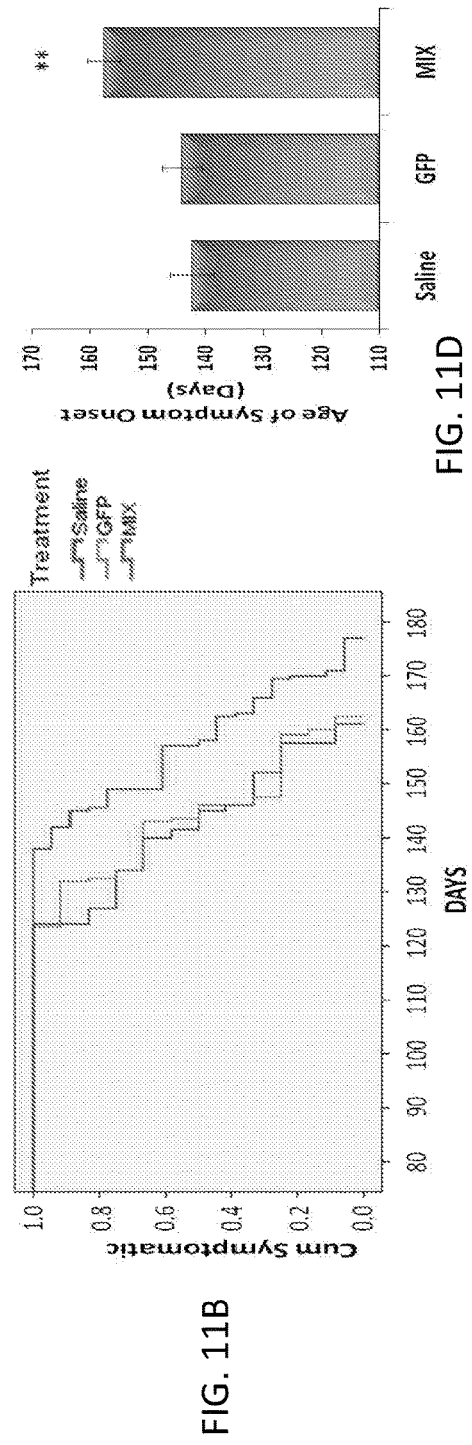

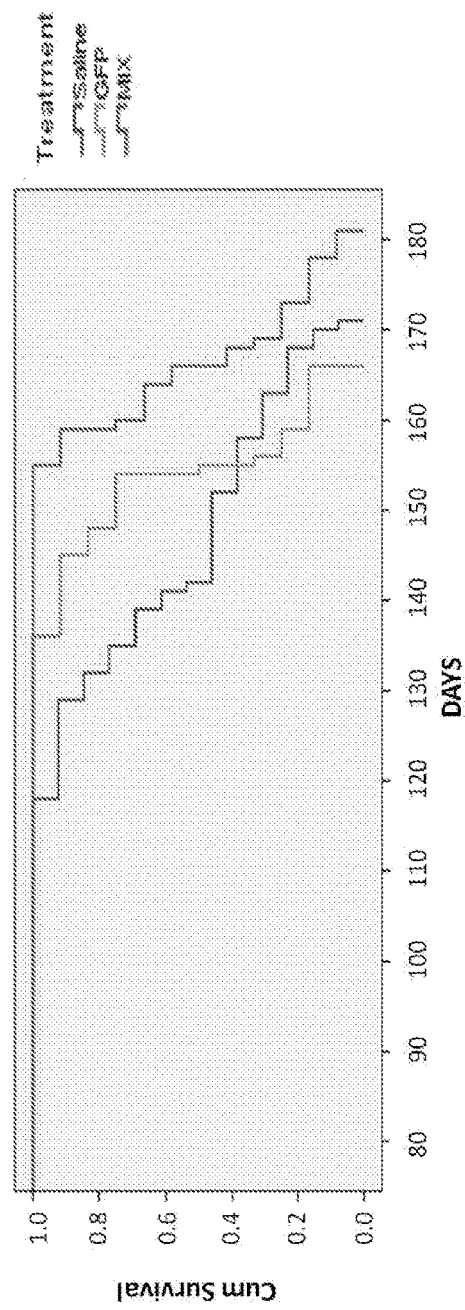
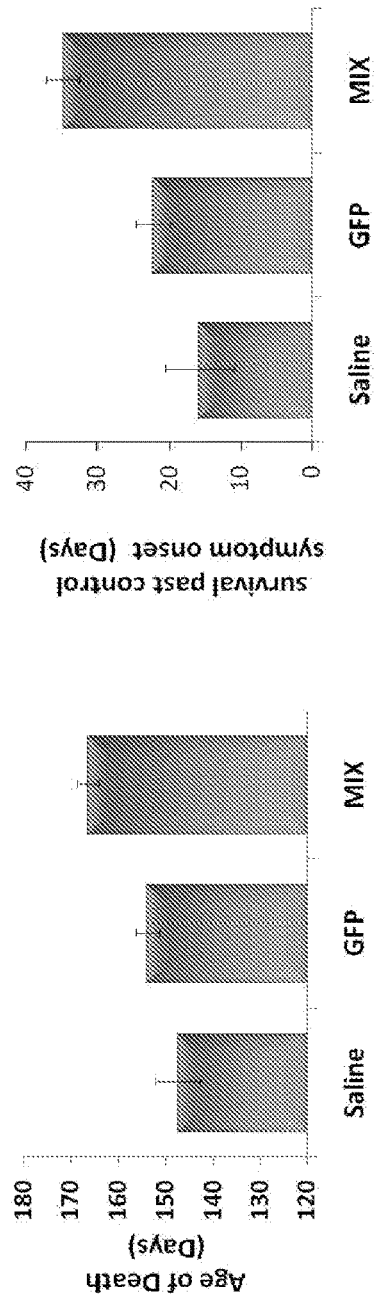
FIG. 12A
FIG. 12B
FIG. 12C

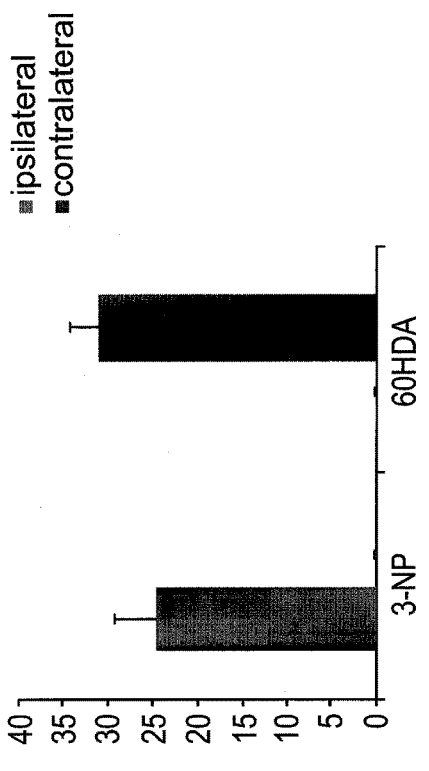
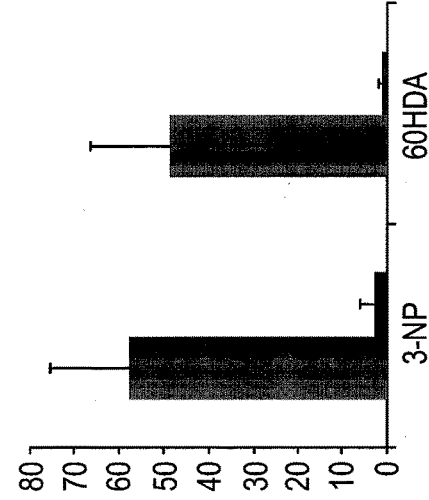

SEQUENCE LISTING

<160> NUMBER OF SEQ ID NOS: 6

<210> SEQ ID NO 1
<211> LENGTH: 605
<212> TYPE: PRT
<213> ORGANISM: Homo sapiens

<400> SEQUENCE: 1

```
Met Met Asp Leu Glu Leu Pro Pro Gly Leu Pro Ser Gln Gln Asp
1               5                   10                  15

Met Asp Leu Ile Asp Ile Leu Trp Arg Gln Asp Ile Asp Leu Gly Val
                20                  25                  30

Ser Arg Glu Val Phe Asp Phe Ser Gln Arg Arg Lys Glu Tyr Glu Leu
            35                  40                  45

Glu Lys Gln Lys Lys Leu Glu Lys Glu Arg Gln Glu Gln Leu Gln Lys
        50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220
```

Asn Tyr His Phe Tyr Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
275                 280                 285

Phe Ile Ala Glu Pro Ser Ile Ser Asn Ser Met Pro Ser Pro Ala Thr
290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
            325                 330                 335

Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Tyr Gly Asp
            355                 360                 365

Thr Leu Leu Gly Leu Ser Asp Ser Glu Val Glu Glu Leu Asp Ser Ala
370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415

Val His Asp Ala Gln Cys Glu Asn Thr Pro Gly Lys Glu Leu Pro Val
            420                 425                 430

Ser Pro Gly His Arg Lys Thr Pro Phe Thr Lys Asp Lys His Ser Ser
            435                 440                 445

Arg Leu Glu Ala His Leu Thr Arg Asp Glu Leu Arg Ala Lys Ala Leu
450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Gly Lys Asn Lys Val Ala Ala Gln
            500                 505                 510

Asn Cys Arg Lys Arg Lys Leu Glu Asn Ile Val Glu Leu Glu Gln Asp
            515                 520                 525

Leu Asp His Leu Lys Asp Glu Lys Glu Lys Leu Leu Lys Glu Lys Gly
530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575

Ser Pro Ser Glu Tyr Ser Leu Gln Gln Thr Arg Asp Gly Asn Val Phe
            580                 585                 590

Leu Val Pro Lys Ser Lys Lys Pro Asp Val Lys Lys Asn
595                 600                 605

<210> SEQ ID NO 2
<211> LENGTH: 1818
<212> TYPE: DNA
<213> ORGANISM: Homo sapiens

<400> SEQUENCE: 2

```
atgatggact tggagctgcc gccgccggga ctcccgtccc agcaggacat ggatttgatt    60
gacatacttt ggaggcaaga tatagatctt ggagtaagtc gagaagtatt tgacttcagt   120
cagcgacgga aagagtatga gctggaaaaa cagaaaaaac ttgaaaagga agacaagaa    180
caactccaaa aggagcaaga gaaagccttt ttcgctcagt tacaactaga tgaagagaca   240
ggtgaatttc tcccaattca gccagccag cacatccagt cagaaaccag tggatctgcc    300
aactactccc aggttgccca cattcccaaa tcagatgctt tgtactttga tgactgcatg   360
cagcttttgg cgcagacatt cccgtttgta gatgacaatg aggtttcttc ggctacgttt   420
cagtcacttg ttcctgatat tcccggtcac atcgagagcc cagtcttcat tgctactaat   480
caggctcagt cacctgaaac ttctgttgct caggtagccc tgttgattt agacggtatg    540
caacaggaca ttgagcaagt ttgggaggag ctattatcca ttcctgagtt acagtgtctt   600
aatattgaaa atgacaagct ggttgagact accatggttc caagtccaga agccaaactg   660
acagaagttg acaattatca tttttactca tctataccct caatggaaaa agaagtaggt   720
aactgtagtc cacattttct taatgctttt gaggattcct tcagcagcat cctctccaca   780
gaagacccca accagttgac agtgaactca ttaaattcag atgccacagt caacacagat   840
tttggtgatg aatttatc tgctttcata gctgagccca gtatcagcaa cagcatgccc    900
tcacctgcta ctttaagcca ttcactctct gaacttctaa atgggcccat tgatgtttct   960
gatctatcac tttgcaaagc tttcaaccaa accaccctg aaagcacagc agaattcaat   1020
gattctgact ccggcatttc actaaacaca agtcccagtg tggcatcacc agaacactca   1080
gtggaatctt ccagctatgg agacacacta cttggcctca gtgattctga agtggaagag   1140
ctagatagtg cccctggaag tgtcaaacag aatggtccta aaacaccagt acattcttct   1200
ggggatatgg tacaacccct tgtcaccatc t caggggcaga gcactcacgt gcatgatgcc   1260
caatgtgaga cacaccaga aaagaattg cctgtaagtc ctggtcatcg aaaaccccca    1320
ttcacaaaag acaaacattc aagccgcttg gaggctcatc tcacaagaga tgaacttagg   1380
gcaaaagctc tccatatccc attccctgta gaaaaaatca ttaacctccc tgttgttgac   1440
ttcaacgaaa tgatgtccaa agagcagttc aatgaagctc aacttgcatt aattcgggat   1500
atacgtagga ggggtaagaa taaagtggct gctcagaatt gcagaaaaag aaaactggaa   1560
aatatagtag aactagagca agatttagat catttgaaag atgaaaaga aaaattgctc    1620
aaagaaaaag gagaaaatga caaaagcctt cacctactga aaaaacaact cagcaccta    1680
tatctcgaag ttttcagcat gctacgtgat gaagatggaa aaccttattc tcctagtgaa   1740
tactcctgc agcaaacaag agatggcaat gttttccttg ttcccaaaag taagaagcca   1800
gatgttaaga aaaactag                                                  1818
```

<210> SEQ ID NO 3
<211> LENGTH: 574
<212> TYPE: PRT
<213> ORGANISM: Homo sapiens

<400> SEQUENCE: 3

Met Ala Ser Thr Glu Gly Ala Asn Asn Met Pro Lys Gln Val Glu Val
1               5                   10                  15

Arg Met His Asp Ser His Leu Gly Ser Glu Glu Pro Lys His Arg His
            20                  25                  30

Leu Gly Leu Arg Leu Cys Asp Lys Leu Gly Lys Asn Leu Leu Leu Thr
        35                  40                  45

```
Leu Thr Val Phe Gly Val Ile Leu Gly Ala Val Cys Gly Gly Leu Leu
    50                  55                  60

Arg Leu Ala Ser Pro Ile His Pro Asp Val Val Met Leu Ile Ala Phe
 65                  70                  75                  80

Pro Gly Asp Ile Leu Met Arg Met Leu Lys Met Leu Ile Leu Pro Leu
                    85                  90                  95

Ile Ile Ser Ser Leu Ile Thr Gly Leu Ser Gly Leu Asp Ala Lys Ala
                100                 105                 110

Ser Gly Arg Leu Gly Thr Arg Ala Met Val Tyr Tyr Met Ser Thr Thr
                115                 120                 125

Ile Ile Ala Ala Val Leu Gly Val Ile Leu Val Leu Ala Ile His Pro
                130                 135                 140

Gly Asn Pro Lys Leu Lys Lys Gln Leu Gly Pro Gly Lys Lys Asn Asp
145                 150                 155                 160

Glu Val Ser Ser Leu Asp Ala Phe Leu Asp Leu Ile Arg Asn Leu Phe
                165                 170                 175

Pro Glu Asn Leu Val Gln Ala Cys Phe Gln Gln Ile Gln Thr Val Thr
                180                 185                 190

Lys Lys Val Leu Val Ala Pro Pro Asp Glu Glu Ala Asn Ala Thr
                195                 200                 205

Ser Ala Val Val Ser Leu Leu Asn Glu Thr Val Thr Glu Val Pro Glu
210                 215                 220

Glu Thr Lys Met Val Ile Lys Lys Gly Leu Glu Phe Lys Asp Gly Met
225                 230                 235                 240

Asn Val Leu Gly Leu Ile Gly Phe Phe Ile Ala Phe Gly Ile Ala Met
                245                 250                 255

Gly Lys Met Gly Asp Gln Ala Lys Leu Met Val Asp Phe Phe Asn Ile
                260                 265                 270

Leu Asn Glu Ile Val Met Lys Leu Val Ile Met Ile Met Trp Tyr Ser
                275                 280                 285

Pro Leu Gly Ile Ala Cys Leu Ile Cys Gly Lys Ile Ala Ile Lys
290                 295                 300

Asp Leu Glu Val Val Ala Arg Gln Leu Gly Met Tyr Met Val Thr Val
305                 310                 315                 320

Ile Ile Gly Leu Ile Ile His Gly Gly Ile Phe Leu Pro Leu Ile Tyr
                325                 330                 335

Phe Val Val Thr Arg Lys Asn Pro Phe Ser Phe Phe Ala Gly Ile Phe
                340                 345                 350

Gln Ala Trp Ile Thr Ala Leu Gly Thr Ala Ser Ser Ala Gly Thr Leu
                355                 360                 365

Pro Val Thr Phe Arg Cys Leu Glu Glu Asn Leu Gly Ile Asp Lys Arg
                370                 375                 380

Val Thr Arg Phe Val Leu Pro Val Gly Ala Thr Ile Asn Met Asp Gly
385                 390                 395                 400

Thr Ala Leu Tyr Glu Ala Val Ala Ala Ile Phe Ile Ala Gln Met Asn
                405                 410                 415

Gly Val Val Leu Asp Gly Gly Gln Ile Val Thr Val Ser Leu Thr Ala
                420                 425                 430

Thr Leu Ala Ser Val Gly Ala Ala Ser Ile Pro Ser Ala Gly Leu Val
                435                 440                 445

Thr Met Leu Leu Ile Leu Thr Ala Val Gly Leu Pro Thr Glu Asp Ile
                450                 455                 460
```

```
Ser Leu Leu Val Ala Val Asp Trp Leu Leu Asp Arg Met Arg Thr Ser
465                 470                 475                 480

Val Asn Val Val Gly Asp Ser Phe Gly Ala Gly Ile Val Tyr His Leu
            485                 490                 495

Ser Lys Ser Glu Leu Asp Thr Ile Asp Ser Gln His Arg Val His Glu
        500                 505                 510

Asp Ile Glu Met Thr Lys Thr Gln Ser Ile Tyr Asp Asp Met Lys Asn
    515                 520                 525

His Arg Glu Ser Asn Ser Asn Gln Cys Val Tyr Ala Ala His Asn Ser
        530                 535                 540

Val Ile Val Asp Glu Cys Lys Val Thr Leu Ala Ala Asn Gly Lys Ser
545                 550                 555                 560

Ala Asp Cys Ser Val Glu Glu Glu Pro Trp Lys Arg Glu Lys
                565                 570

<210> SEQ ID NO 4
<211> LENGTH: 1725
<212> TYPE: DNA
<213> ORGANISM: Homo sapiens

<400> SEQUENCE: 4
atggcatcta cggaaggtgc caacaatatg cccaagcagg tggaagtgcg aatgcacgac      60
agtcatcttg gctcagagga acccaagcac cggcacctgg gcctgcgcct gtgtgacaag     120
ctggggaaga atctgctgct caccctgacg gtgtttggtg tcatcctggg agcagtgtgt     180
ggagggcttc ttcgcttggc atctcccatc caccctgatg tggttatgtt aatagccttc     240 ccagggggata tactcatgag gatgctaaaa atgctcattc ccctctaat catctccagc     300 ttaatcacag ggttgtcagg cctggatgct aaggctagtg gccgcttggg cacgagagcc     360
atggtgtatt acatgtccac gaccatcatt gctgcagtac tgggggtcat tctggtcttg     420
gctatccatc caggcaatcc caagctcaag aagcagctgg ggcctgggaa gaagaatgat     480
gaagtgtcca gcctggatgc cttcctggac cttattcgaa atctcttccc tgaaaacctt     540
gtccaagcct gctttcaaca gattcaaaca gtgacgaaga agtcctggt tgcaccaccg     600 ccggacgagg aggccaacgc aaccagcgct gttgtctctc tgttgaacga gactgtgact     660
gaggtgccgg aggagactaa gatggttatc aagaagggcc tggagttcaa ggatgggatg     720
aacgtcttag gtctgatagg gttttttcatt gcttttggca tcgctatggg gaagatggga     780
gatcaggcca gctgatggt ggatttcttc aacattttga tgagattgt aatgaagtta     840 gtgatcatga tcatgtggta ctctccctg ggtatcgcct gcctgatctg tggaaagatc     900
attgcaatca aggacttaga agtggttgct aggcaactgg ggatgtacat ggtaacagtg     960
atcataggcc tcatcatcca cggggggcatc tttctcccct tgatttactt tgtagtgacc    1020 aggaaaaaacc ccttctcctt ttttgctggc attttccaag cttggatcac tgccctgggc    1080
accgcttcca gtgctggaac tttgcctgtc acctttcgtt gcctggaaga aaatctgggg    1140
attgataagc gtgtgactag attcgtcctt cctgttggag caaccattaa catggatggt    1200
acagcccttt atgaagcggt agccgccatc tttatagccc aaatgaatgg tgttgtcctg    1260 gatgaggac agattgtgac tgtaagcctc acagccaccc tggcaagcgt cggcgcggcc    1320
agtatcccca gtgccgggct ggtcaccatg ctcctcattc tgacagccgt gggcctgcca    1380
acagaggaca tcagcctgct ggtggctgtg actggctgc tggacaggat gagaacttca    1440
gtcaatgttg tgggtgactc ttttggggct gggatagtct atcacctctc caagtctgag    1500
```

```
ctggatacca ttgactccca gcatcgagtg catgaagata ttgaaatgac caagactcaa    1560
tccatttatg atgacatgaa gaaccacagg gaaagcaact ctaatcaatg tgtctatgct    1620
gcacacaact ctgtcatagt agatgaatgc aaggtaactc tggcagccaa tggaaagtca    1680
gccgactgca gtgttgagga agaaccttgg aaacgtgaga aatag                    1725
```

<210> SEQ ID NO 5
<211> LENGTH: 558
<212> TYPE: PRT
<213> ORGANISM: Homo sapiens

<400> SEQUENCE: 5

```
Met Tyr Arg Tyr Leu Ala Lys Ala Leu Leu Pro Ser Arg Ala Gly Pro
1               5                   10                  15

Ala Ala Leu Gly Ser Ala Ala Asn His Ser Ala Ala Leu Leu Gly Arg
            20                  25                  30

Gly Arg Gly Gln Pro Ala Ala Ala Ser Gln Pro Gly Leu Ala Leu Ala
        35                  40                  45

Ala Arg Arg His Tyr Ser Glu Leu Val Ala Asp Arg Glu Asp Asp Pro
    50                  55                  60

Asn Phe Phe Lys Met Val Glu Gly Phe Phe Asp Arg Gly Ala Ser Ile
65                  70                  75                  80

Val Glu Asp Lys Leu Val Lys Asp Leu Arg Thr Gln Glu Ser Glu Glu
                85                  90                  95

Gln Lys Arg Asn Arg Val Arg Gly Ile Leu Arg Ile Ile Lys Pro Cys
            100                 105                 110

Asn His Val Leu Ser Leu Ser Phe Pro Ile Arg Arg Asp Asp Gly Ser
        115                 120                 125

Trp Glu Val Ile Glu Gly Tyr Arg Ala Gln His Ser Gln His Arg Thr
    130                 135                 140

Pro Cys Lys Gly Gly Ile Arg Tyr Ser Thr Asp Val Ser Val Asp Glu
145                 150                 155                 160

Val Lys Ala Leu Ala Ser Leu Met Thr Tyr Lys Cys Ala Val Val Asp
                165                 170                 175

Val Pro Phe Gly Gly Ala Lys Ala Gly Val Lys Ile Asn Pro Lys Asn
            180                 185                 190

Tyr Thr Glu Asn Glu Leu Glu Lys Ile Thr Arg Arg Phe Thr Met Glu
        195                 200                 205

Leu Ala Lys Lys Gly Phe Ile Gly Pro Gly Val Asp Val Pro Ala Pro
    210                 215                 220

Asp Met Asn Thr Gly Glu Arg Glu Met Ser Trp Ile Ala Asp Thr Tyr
225                 230                 235                 240

Ala Ser Thr Ile Gly His Tyr Asp Ile Asn Ala His Ala Cys Val Thr
                245                 250                 255

Gly Lys Pro Ile Ser Gln Gly Gly Ile His Gly Arg Ile Ser Ala Thr
            260                 265                 270

Gly Arg Gly Val Phe His Gly Ile Glu Asn Phe Ile Asn Glu Ala Ser
        275                 280                 285

Tyr Met Ser Ile Leu Gly Met Thr Pro Gly Phe Arg Asp Lys Thr Phe
    290                 295                 300

Val Val Gln Gly Phe Gly Asn Val Gly Leu His Ser Met Arg Tyr Leu
305                 310                 315                 320

His Arg Phe Gly Ala Lys Cys Ile Ala Val Gly Glu Ser Asp Gly Ser
                325                 330                 335
```

```
Ile Trp Asn Pro Asp Gly Ile Asp Pro Lys Glu Leu Glu Asp Phe Lys
                340                 345                 350

Leu Gln His Gly Ser Ile Leu Gly Phe Pro Lys Ala Lys Pro Tyr Glu
        355                 360                 365

Gly Ser Ile Leu Glu Val Asp Cys Asp Ile Leu Ile Pro Ala Ala Thr
    370                 375                 380

Glu Lys Gln Leu Thr Lys Ser Asn Ala Pro Arg Val Lys Ala Lys Ile
385                 390                 395                 400

Ile Ala Glu Gly Ala Asn Gly Pro Thr Thr Pro Glu Ala Asp Lys Ile
                405                 410                 415

Phe Leu Glu Arg Asn Ile Leu Val Ile Pro Asp Leu Tyr Leu Asn Ala
            420                 425                 430

Gly Gly Val Thr Val Ser Tyr Phe Glu Trp Leu Lys Asn Leu Asn His
        435                 440                 445

Val Ser Tyr Gly Arg Leu Thr Phe Lys Tyr Glu Arg Asp Ser Asn Tyr
    450                 455                 460

His Leu Leu Leu Ser Val Gln Glu Ser Leu Glu Arg Lys Phe Gly Lys
465                 470                 475                 480

His Gly Gly Thr Ile Pro Ile Val Pro Thr Ala Glu Phe Gln Asp Ser
                485                 490                 495

Ile Ser Gly Ala Ser Glu Lys Asp Ile Val His Ser Ala Leu Ala Tyr
            500                 505                 510

Thr Met Glu Arg Ser Ala Arg Gln Ile Met His Thr Ala Met Lys Tyr
        515                 520                 525

Asn Leu Gly Leu Asp Leu Arg Thr Ala Ala Tyr Val Asn Ala Ile Glu
    530                 535                 540

Lys Val Phe Lys Val Tyr Ser Glu Ala Gly Val Thr Phe Thr
545                 550                 555
```

<210> SEQ ID NO 6
<211> LENGTH: 1677
<212> TYPE: DNA
<213> ORGANISM: Homo sapiens

<400> SEQUENCE: 6

```
atgtaccgct acctggccaa agcgctgctg ccgtcccggg ccgggcccgc tgccctgggc      60
tccgcggcca accactcggc cgcgttgctg ggcggggcc gcggacagcc cgccgccgcc     120
tcgcagccgg ggctcgcatt ggccgcccgg cgccactaca gcgagttggt ggccgaccgc     180
gaggacgacc ccaacttctt caagatggtg gagggcttct tcgatcgcgg cgccagcatc     240
gtggaggaca agttggtgaa ggacctgagg acccaggaaa gcgaggagca gaagcggaac     300
cgggtgcgcg catcctgcg gatcatcaag ccctgcaacc atgtgctgag tctctccttc     360
cccatccggc gcgacgacgg ctcctgggag gtcatcgaag ctaccgggc ccagcacagc     420
cagcaccgca cgccctgcaa ggaggtatc cgttacagca ctgatgtgag tgtagatgaa     480
gtaaaagctt tggcttctct gatgacatac aagtgtgcag tggttgatgt gccgtttggg     540
ggtgctaaag ctggtgttaa gatcaatccc aagaactata ccgaaaatga attggaaaag     600
atcacaagga ggttcaccat ggagctagca aagaagggct ttattggtcc tggcgttgat     660
gtgcctgctc agacatgaa cacaggtgag cgggagatgt cctggattgc tgataccat     720
gccagcacca tagggcacta tgatattaat gcacacgcct gttactgg taaacccatc     780
agccaagggg gaatccatgg acgcatctct gctactggcc gtggtgtctt ccatgggatt     840
gaaaacttca tcaatgaagc ttccttacatg agcatttag gaatgacacc agggtttaga     900
```

```
gataaaacat ttgttgttca gggatttggt aatgtgggcc tacactctat gagatattta    960
catcgttttg gtgctaaatg tattgctgtt ggtgagtctg atgggagtat atggaatcca   1020
gatggtattg acccaaagga actggaagac ttcaaattgc aacatgggtc cattctgggc   1080
ttccccaagg caaagcccta tgaaggaagc atcttggagg tcgactgtga catactgatc   1140
ccagctgcca ctgagaagca gttgaccaaa tccaacgcac ccagagtcaa agccaagatc   1200
attgctgaag gtgccaatgg gccaacaact ccagaagctg ataagatctt cctggagaga   1260
aacattttgg ttattccaga tctctacttg aatgctggag gagtgacagt atcttacttt   1320
gagtggctga agaatctaaa tcatgtcagc tatggccgtt tgaccttcaa atatgaaagg   1380
gattctaact accacttgct cctgtctgtt caagagagtt tagaaagaaa atttggaaag   1440
catggtggaa ctattcccat tgtacccacg gcagagttcc aagacagtat atcgggtgca   1500
tctgagaaag acattgtgca ctctgccttg gcatacacaa tggagcgttc tgccaggcaa   1560
attatgcaca cagccatgaa gtataacctg ggattggacc tgagaacagc tgcctatgtc   1620
aatgccattg aaaaagtctt caaagtgtac agtgaagctg gtgtgacctt cacatag     1677
```

COMBINATION TREATMENT FOR AMYOTROPHIC LATERAL SCLEROSIS (ALS)

DETAILS OF RELATED APPLICATIONS

This application is a national stage application under 35 U.S.C. § 371 of PCT /IL2013/050943 filed on 14 Nov. 2013 and subsequently published as WO/2014/076702 on 22 May 2014, said PCT application claiming the benefit of US provisional application 61/726,050 filed on 14 Nov. 2013 according to 35U.S.C. § 119 (e).

FIELD AND BACKGROUND OF THE INVENTION

The present invention, in some embodiments thereof, relates to a composition comprising at least two active agents for the treatment of diseases and, more particularly, but not exclusively, to neurodegenerative diseases.

Amyotrophic Lateral Sclerosis (ALS) is a fatal, rapidly progressive, neurodegenerative disease characterized by loss of motor neurons in the motor cortex, brainstem and spinal cord. This motor neuron degeneration results in weakness, muscle atrophy, fasciculations and paralysis, a process culminating in death due to respiratory failure within 2-5 years of clinical onset (Charles and Swash, 2001; Oliveira and Pereira, 2009). Despite extensive efforts the underlying cause of ALS and the path of neurodegeneration remain elusive. This led to the proposal of numerous hypotheses including; reduced neurotrophic factor secretion, mitochondrial dysfunction, toxic intracellular aggregations and axonal impairment due to neurofilament accumulation (Benkler et al., 2010; Lev et al., 2009; Offen et al., 2009; Rothstein, 2009; Van Damme et al., 2005; Xiao et al., 2006). One of the currently most prominent pathophysiological hypotheses explaining ALS progression involves glutamate excitotoxicity and oxidative stress (Bogaert et al, 2010; Rothstein, 2009; Van Damme et al. 2005).

Preventing or slowing motor neuron degeneration and death in ALS are critical goals of future therapies.

The selective motor neuron death which occurs in ALS led researchers to explore cell autonomous mechanisms. However, studies performed in the SOD1 fALS mouse model suggest that non-neuronal cells such as astrocytes and microglia might be at play (Ilieva et al., 2009; Yamanaka et al., 2008; Di Giorgio et al., 2007; Beers et al., 2006; Boillée et al., 2006; Clement et al., 2003).

Astrocytes play a crucial role in the function and survival of motor neurons through numerous mechanisms, among them are secretion of neurotrophic factors, maintenance of synaptic glutamate homeostasis and modulation of the neuronal susceptibility to glutamate excitotoxicity. Increasing evidence indicate astrocytic dysfunction in all three mechanisms may well be instrumental in the pathogenesis of ALS (Van Den Bosch and Robberecht, 2008; Staats and Van Den Bosch, 2009). Under physiological conditions astrocytes are activated by stress signals from their environment. Altered response to those stress signals may prove harmful to the wellbeing of the CNS. It was found that astrocytes derived from the SOD1 G93A ALS mouse model exhibit a reduced glutamatergic and trophic response to specific activations compared to their wild-type counterparts. Wild-type astrocytes exhibited a robust response when activated with lipopolysaccharide (LPS), G5 or treated with ceftriaxone in many parameters evaluated.

These parameters include increased expression of GLT-1 and GLAST the two major astrocytic glutamate transporters, accompanied by a marked increase in the astrocytic glutamate clearance and up-regulation of neurotrophic factor expression. However, not only do un-treated SOD1 G93A astrocytes take up glutamate less efficiently, but in response to activation they show no further increase in any of the glutamatergic parameters evaluated. Furthermore, activation of wild-type astrocytes, but not SOD1 G93A astrocytes, improved their ability to protect the motor neuron cell line NSC-34 from glutamate induced excitotoxicity. Such data indicates that altered astrocyte activation may well be pivotal to the pathogenesis of ALS.

It has been proposed that the reduced glutamatergic and trophic response of astrocytes to activation in ALS, may, over time, lead to disruption of glutamate homeostasis and accumulative CNS damage, thus facilitating motor neuron degeneration.

Glutamate is the main excitatory amino acid (a.a) neurotransmitter in the human central nervous system (CNS). It plays a major role in learning, development, synaptic plasticity, cognitive functions and behavior (Danbolt, 2001; Maragakis and Rothstein, 2001; Mattson, 2008; Molz et al., 2008). However, overstimulation of glutamate receptors leads to neuronal degeneration, a process commonly referred to as glutamate excitotoxicity (Attwell, 2000; Bogaert et al, 2010; Brown, 2000; Danbolt, 2001; de Hemptinne et al. 2004; Foran and Trotti, 2009; Lee et al., 2007; Mattson, 2008; Maragakis and Rothstein, 2001; Sheldon and Robinson, 2007; Sonnewald et al., 2002; Van Damme et al., 2005).

Abnormal glutamate metabolism accompanied by selective loss of the astroglial glutamate transporter-1 GLT-1 (and its human counterpart EAAT2) were observed in sporadic and familial ALS patients as well as in mutant SOD1 animal models (Rothstein et al., 1992; Rothstein et al., 1995; Bendotti et al., 2001). Furthermore, both in vitro and in vivo experiments demonstrate that selective loss of GLT-1 can lead to motor neuron degeneration (Rothstein et al., 1996).

Glutamate excitotoxicity can lead to secondary oxidative stress which in turn causes severe motor neuron injury and death (Lynch and Guttmann, 2002). NRF2 is a transcription factor which activates genes containing the antioxidant response element (ARE), thus constituting a major node in the cellular anti-oxidative response (Hybertson et al., 2011; Vargas and Johnson, 2009). It has been previously shown that activation of NRF2 specifically in astrocytes protects neurons from a variety of in vitro insults as well as conveys protection in an ALS mouse model (Calkins et al., 2010; Kraft et al., 2004; Shih et al., 2003; Vargas et al., 2006, 2008 and 2009).

Riluzole has been approved for the treatment of ALS. Its mechanism of action may be partly due the prevention of stimulation of glutamate receptors. It may be provided alone or together with antioxidants such as vitamin C or E.

U.S. Application No. 20090304661 teaches administration of glutamate modifying enzymes and stress hormone modulating agents for the treatment of neurodegenerative diseases.

U.S. Application No. 20110250300 teaches administration of agents that cause the upregulation of Nrf2 for the treatment of neurodegenerative diseases.

Rothstein, J. D., Martin, L. J., and Kuncl, R. W. (1992). N. Engl. J. Med. 326, 1464-1468; Rothstein, J. D., Jin, L., Dykes-Hoberg, M., and Kuncl, R. W. (1993). Proc. Natl. Acad. Sci. USA 90, 6591-6595; Rothstein, J. D., Martin, L., Levey, A. I., Dykes-Hoberg, M., Jin, L., Wu, D., Nash, N., and Kuncl, R. W. (1994) Neuron 13, 713-725 teach that EAAT2 is dysfunctional in ALS patients.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C: Activation enhanced [$^3$H] D-aspartate uptake in astrocytes derived from wild-type but not SOD1 G93A mice. (A) Saturation curves for [$^3$H] D-aspartate (5-1,000 μM) uptake into astrocyte cultures prepared from wild-type and SOD1 G93A mice. (B) Uptake of [$^3$H] D-aspartate (40 μM) in wild-type and SOD1 G93A astrocyte cultures and the effect of uptake inhibition by incubation in sodium-free buffer (Na$^+$ free) or by exposure to the uptake inhibitor t-PDC (0.314 μM). (C) The effect of activation with G5 (1:100), LPS (1 μg/mL) and CEF (10 μM) for 48 h on the [$^3$H] D-aspartate (40 μM) uptake in wild-type and SOD1 G93A astrocyte cultures. *P<0.05; P<0.01, *P<0.001 as compared with control.

FIGS. 2A-K illustrate results following transfection of SOD1 G93A astrocytes with lentiviral vectors. Light microscopy images of control un-transected cells (A) and GFP transfected (B) SOD1 G93A astrocytes. astrocytic viability following transfection (C). Astrocytic EAAT2 mRNA expression levels following transfection with lentiviral vectors encoding for EAAT2 (D) astrocytic glutamate uptake velocity (E). astrocytic GDH2 mRNA expression levels following transfection with lentiviral vectors encoding for GDH2 (F) astrocytic GDH2 activity (G). astrocytic NRF2 mRNA expression levels following transfection with lentiviral vectors encoding for NRF2 (H) astrocytic NRF2 activity (I). mRNA expression levels of two NRF2 downstream genes; GCLM (J) and NQO1(K) following transfection with lentiviral vectors encoding for NRF2. A,B scale bar: 100 μm. *p<0.05, p<0.01, *p<0.001.

FIG. 3B represents percentage difference added by various combinations of transduced genes. Percent of cell viability was calculated as the percentage of NSC-34D viability co-cultured with transduced astrocytes and exposed to excite-oxidative insult as compared to NSC-34 cell viability when not exposed to astrocytes or insult.

FIG. 5 is a schematic representation of the experimental design depicting the administration of treatment in relation to the disease progression.

FIGS. 6A-D are bar graphs illustrating combined treatment with EAAT2, NRF2 and GDH2 has a therapeutic effect not achieved by treatment with each gene individually. Combined treatment preserved male (A) and female (B) neurological score and body weight (C, D respectively). *P<0.05, **P<0.001 as determined by ANOVA.

FIGS. 11A-D are graphs illustrating that treatment with EAAT2, NRF2 and GDH2 containing lentiviruses delays the onset of symptoms in SOD1 G93A ALS mice. The mice were injected with saline, lentiviruses containing GFP or a mixture of three types of lentiviruses each containing one of the three genes; EAAT2, NRF2 or GDH2 (MIX). Onset of symptoms in male (A) and female (B) mice (for MIX P<0.05 as determined by Kaplan-Meier). Male (C) and female (D) mean age of symptom onset (*P<0.05, **P<0.01 as determined by ANOVA). 12<n>17 animals per group per gender.

FIGS. 12A-F are graphs illustrating treatment with EAAT2, NRF2 and GDH2 containing lentiviruses prolongs the survival of SOD1 G93A ALS mice. The mice were injected with saline, lentiviruses containing GFP or a mixture of three types of lentiviruses each containing one of the three genes; EAAT2, NRF2 or GDH2 (MIX). Survival of male (A) and female (D) mice (for MIX P<0.005 as determined by Kaplan-Meier). Male (B) and female (E) mean age at death (*P<0.001 as determined by ANOVA). Average number of days the male (C) and female (F) mice survived past the symptom onset of saline treated mice (*P<0.001 as determined by ANOVA). 12<n>17 animals per group per gender.

FIGS. 16A-B are graphs illustrating the effect of 3-NP and 6-OHDA administration on the number of ipsilateral and contralateral rotations following amphetamine administration (FIG. 16A) or apomorphine administration (FIG. 16B).

SUMMARY OF THE INVENTION

Figure 2C:
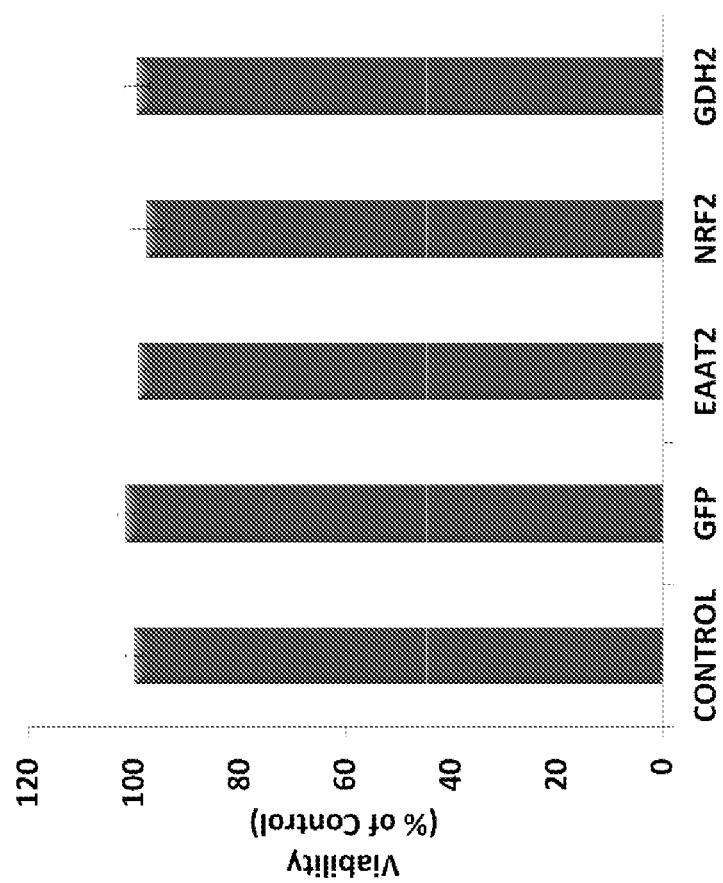

According to an aspect of some embodiments of the present invention there is provided a method of treating a disease selected from the group consisting of emphysema, sepsis, septic shock, ischemic injury, cerebral ischemia, a neurodegenerative disorder, meningitis, encephalitis, hemorrhage, cerebral ischemia, heart ischemia and a cognitive deficit in a subject in need thereof comprising administering to the subject a therapeutically effective amount of a combination of at least two agents, wherein a first of the two agents upregulates an activity and/or expression of Nuclear factor (erythroid-derived 2)-like 2 (Nrf2) and a second of the two agents is a glutamatergic modulator, thereby treating the disease.

According to an aspect of some embodiments of the present invention there is provided a method of treating a disease selected from the group consisting of emphysema, sepsis, septic shock, ischemic injury, cerebral ischemia, a neurodegenerative disorder, meningitis, encephalitis, hemorrhage, cerebral ischemia, heart ischemia and a cognitive deficit in a subject in need thereof comprising administering to the subject a therapeutically effective amount of a combination of at least three agents, wherein a first of the three agents upregulates an activity and/or expression of EAAT2, a second of the three agents upregulates an activity and/or expression of glutamate dehydrogenase and a third of the three agents is an antioxidant, thereby treating the disease.

According to an aspect of some embodiments of the present invention there is provided a method of treating a disease selected from the group consisting of emphysema, sepsis, septic shock, ischemic injury, cerebral ischemia, a neurodegenerative disorder, meningitis, encephalitis, hemorrhage, cerebral ischemia, heart ischemia and a cognitive deficit in a subject in need thereof comprising administering to the subject a therapeutically effective amount of a combination of at least three agents, wherein a first of the three agents upregulates an activity and/or expression of EAAT2, a second of the three agents upregulates an activity and/or expression of glutamate dehydrogenase and a third of the three agents upregulates an activity and/or expression of Nrf2, thereby treating the disease.

According to an aspect of some embodiments of the present invention there is provided an article of manufacture comprising at least two agents, wherein a first of the at least two agents upregulates an activity and/or expression of Nrf2 and a second of the at least two agents is a glutamatergic modulator.

According to an aspect of some embodiments of the present invention there is provided an article of manufacture comprising at least three agents, wherein a first of the three agents upregulates an activity and/or expression of EAAT2, a second of the three agents upregulates an activity and/or expression of glutamate dehydrogenase and a third of the three agents is an antioxidant.

According to an aspect of some embodiments of the present invention there is provided an antioxidant and a glutamatergic modulator for use in treating a disease selected from the group consisting of emphysema, sepsis, septic shock, ischemic injury, cerebral ischemia, a neurodegenerative disorder, meningitis, encephalitis, hemorrhage, cerebral ischemia, heart ischemia and a cognitive deficit.

According to some embodiments of the invention, the neurodegenerative disorder is selected from the group consisting of amyotrophic lateral sclerosis (ALS), multiple system atrophy (MSA), Huntington's disease, Parkinson's disease, Alzheimer's disease and schizophrenia.

According to some embodiments of the invention, the neurodegenerative disorder is ALS or multiple system atrophy (MSA).

According to some embodiments of the invention, the glutamatergic modulator increases an expression and/or activity of a glutamate transporter.

According to some embodiments of the invention, the glutamate transporter is selected from the group consisting of excitatory amino acid transporter 1 (EAAT1), EAAT2, and EAAT3.

According to some embodiments of the invention, the glutamatergic modulator increases an expression and/or activity of least one glutamate modifying enzyme being selected from the group consisting of a transaminase, a dehydrogenase, a decarboxylase, a ligase, an aminomutase, a racemase and a transferase.

According to some embodiments of the invention, the transaminase is selected from the group consisting of glutamate oxaloacetate transaminase, glutamate pyruvate transaminase, acetylornithine transaminase, ornithine-oxo-acid transaminase, succinyldiaminopimelate transaminase, 4-aminobutyrate transaminase, alanine transaminase, (s)-3-amino-2-methylpropionate transaminase, 4-hydroxyglutamate transaminase, diiodotyro sine transaminase, thyroid-hormone transaminase, tryptophan transaminase, diamine transaminase, cysteine transaminase, L-Lysine 6-transaminase, histidine transaminase, 2-aminoadipate transaminase, glycine transaminase, branched-chain-amino-acid transaminase, 5-aminovalerate transaminase, dihydroxyphenylalanine transaminase, tyrosine transaminase, phosphoserine transaminase, taurine transaminase, aromatic-amino-acid transaminase, aromatic-amino-acid-glyoxylate transaminase, leucine transaminase, 2-aminohexanoate transaminase, ornithine(lysine) transaminase, kynurenine-oxoglutarate transaminase, D-4-hydroxyphenylglycine transaminase, cysteine-conjugate transaminase, 2,5-diaminovalerate transaminase, histidinol-phosphate transaminase, diaminobutyrate-2-oxoglutarate transaminase, udp-2-acetamido-4-amino-2,4,6-trideoxyglucose transaminase and aspartate transaminase.

According to some embodiments of the invention, the dehydrogenase is a glutamate dehydrogenase.

According to some embodiments of the invention, the glutamate dehydrogenase is glutamate dehydrogenase 2.

According to some embodiments of the invention, the decarboxylase is a glutamate decarboxylase.

According to some embodiments of the invention, the ligase is a glutamate-ethylamine ligase.

According to some embodiments of the invention, the transferase is selected from the group consisting of glutamate n-acetyltransferase and adenylyltransferase.

According to some embodiments of the invention, the aminomutase is a glutamate-1-semialdehyde 2,1-aminomutase.

According to some embodiments of the invention, the first of the at least two agents is a polynucleotide encoding the nrf2.

According to some embodiments of the invention, the second of the at least two agents is a polynucleotide encoding the glutamatergic modulator.

According to some embodiments of the invention, the first and/or the second of the at least two agents is a small molecule agent.

According to some embodiments of the invention, the first and/or the second of the at least two agents is a polynucleotide agent.

According to some embodiments of the invention, the first and/or the second and/or the third of the at least three agents is a small molecule agent.

According to some embodiments of the invention, the first and/or the second and/or the third of the at least three agents is a polynucleotide agent.

According to some embodiments of the invention, the second agent upregulates an expression and/or activity of glutamate dehydrogenase.

According to some embodiments of the invention, the method further comprises administering an additional agent which upregulates an activity and/or expression of EAAT2.

According to some embodiments of the invention, the second agent upregulates an activity and/or expression of EAAT2.

According to some embodiments of the invention, the first agent is a polynucleotide which encodes EAAT2 and the second agent is a polynucleotide which encodes glutamate dehydrogenase.

According to some embodiments of the invention, the antioxidant upregulates an activity and/or expression of Nrf2.

According to some embodiments of the invention, the antioxidant causes dissociation of Keap1 from the Nrf2.

According to some embodiments of the invention, the antioxidant comprises an agent selected from the group consisting of Coenzyme Q10, thiol, ascorbic acid, polyphenol, glutathione, vitamin C, vitamin E, catalase, superoxide dismutase and peroxidase.

According to some embodiments of the invention, the antioxidant is an agent that downregulates an activity and/or expression of Keap1.

According to some embodiments of the invention, the administering is effected via intra-cisternal (I.C.) administration.

According to some embodiments of the invention, the administering is effected via intra-muscular (I.M.) administration.

According to some embodiments of the invention, the method further comprises providing an agent which increases the permeability of the blood brain barrier of the subject prior to the administering.

According to some embodiments of the invention, the agent is mannitol.

According to some embodiments of the invention, the glutamate dehydrogenase comprises glutamate dehydrogenase 2.

According to some embodiments of the invention, the at least two agents are formulated in a single composition.

According to some embodiments of the invention, the at least three agents are formulated in a single composition.

According to some embodiments of the invention, the glutamatergic modulator increases an expression and/or activity of a glutamate transporter.

According to some embodiments of the invention, the glutamate transporter is selected from the group consisting of excitatory amino acid transporter 1 (EAAT1), EAAT2, and EAAT3.

According to some embodiments of the invention, the glutamatergic modulator increases an expression and/or activity of least one glutamate modifying enzyme being selected from the group consisting of a transaminase, a dehydrogenase, a decarboxylase, a ligase, an aminomutase, a racemase and a transferase.

According to some embodiments of the invention, the transaminase is selected from the group consisting of glutamate oxaloacetate transaminase, glutamate pyruvate transaminase, acetylornithine transaminase, ornithine-oxo-acid transaminase, succinyldiaminopimelate transaminase, 4-aminobutyrate transaminase, alanine transaminase, (s)-3-amino-2-methylpropionate transaminase, 4-hydroxyglutamate transaminase, diiodotyro sine transaminase, thyroid-hormone transaminase, tryptophan transaminase, diamine transaminase, cysteine transaminase, L-Lysine 6-transaminase, histidine transaminase, 2-aminoadipate transaminase, glycine transaminase, branched-chain-amino-acid transaminase, 5-aminovalerate transaminase, dihydroxyphenylalanine transaminase, tyrosine transaminase, phosphoserine transaminase, taurine transaminase, aromatic-amino-acid transaminase, aromatic-amino-acid-glyoxylate transaminase, leucine transaminase, 2-aminohexanoate transaminase, ornithine(lysine) transaminase, kynurenine-oxoglutarate transaminase, D-4-hydroxyphenylglycine transaminase, cysteine-conjugate transaminase, 2,5-diaminovalerate transaminase, histidinol-phosphate transaminase, diaminobutyrate-2-oxoglutarate transaminase, udp-2-acetamido-4-amino-2,4,6-trideoxyglucose transaminase and aspartate transaminase.

According to some embodiments of the invention, the dehydrogenase is a glutamate dehydrogenase.

According to some embodiments of the invention, the decarboxylase is a glutamate decarboxylase.

According to some embodiments of the invention, the ligase is a glutamate-ethylamine ligase.

According to some embodiments of the invention, the transferase is selected from the group consisting of glutamate n-acetyltransferase and adenylyltransferase.

According to some embodiments of the invention, the aminomutase is a glutamate-1-semialdehyde 2,1-aminomutase.

According to some embodiments of the invention, the first of the at least two agents is a polynucleotide encoding the nrf2.

According to some embodiments of the invention, the second of the at least two agents is a polynucleotide encoding the glutamatergic modulator.

According to some embodiments of the invention, the first and/or the second of the at least two agents is a small molecule agent.

According to some embodiments of the invention, the second agent upregulates an expression and/or activity of glutamate dehydrogenase.

According to some embodiments of the invention, the article of manufacture further comprises an additional agent which upregulates an activity and/or expression of EAAT2.

According to some embodiments of the invention, the second agent upregulates an activity and/or expression of EAAT2.

According to some embodiments of the invention, the first agent is a polynucleotide which encodes EAAT2 and the second agent is a polynucleotide which encodes glutamate dehydrogenase.

According to some embodiments of the invention, the antioxidant upregulates an activity and/or expression of Nrf2.

According to some embodiments of the invention, the antioxidant causes dissociation of Keap1 from the Nrf2.

According to some embodiments of the invention, the antioxidant comprises an agent selected from the group consisting of Coenzyme Q10, thiol, ascorbic acid, polyphenol, glutathione, vitamin C, vitamin E, catalase, superoxide dismutase and peroxidase.

According to some embodiments of the invention, the antioxidant is an agent that downregulates an activity and/or expression of Keap1.

According to some embodiments of the invention, the neurodegenerative disease is ALS or multiple system atrophy (MSA).

According to some embodiments of the invention, the agent which upregulates an activity and/or expression of Nrf2 is selected from the group consisting of NAD(P)H quinone oxidoreductase 1 (Nqo1), Glutamate-cysteine ligase, catalytic (Gclc), UYglutamate-cysteine ligase, modifier (GCLM), Heme oxygenase-1 (HMOX1, HO-1), glutathione S-transferase (GST), UDP-lucuronosyltransferase (UGT) and Multidrug resistance-associated proteins (Mrps).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to a composition comprising at least two active agents for the treatment of diseases and, more particularly, but not exclusively, to neurodegenerative diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The results provided herein show that a combined treatment with three lentiviral vectors, each containing one of the following three genes; EAAT2, GDH2 and NRF2 delayed symptom onset, preserved body weight and motor function in both an ALS mouse model and a MSA (multiple system atrophy) MSA mouse model.

Figure 12D:
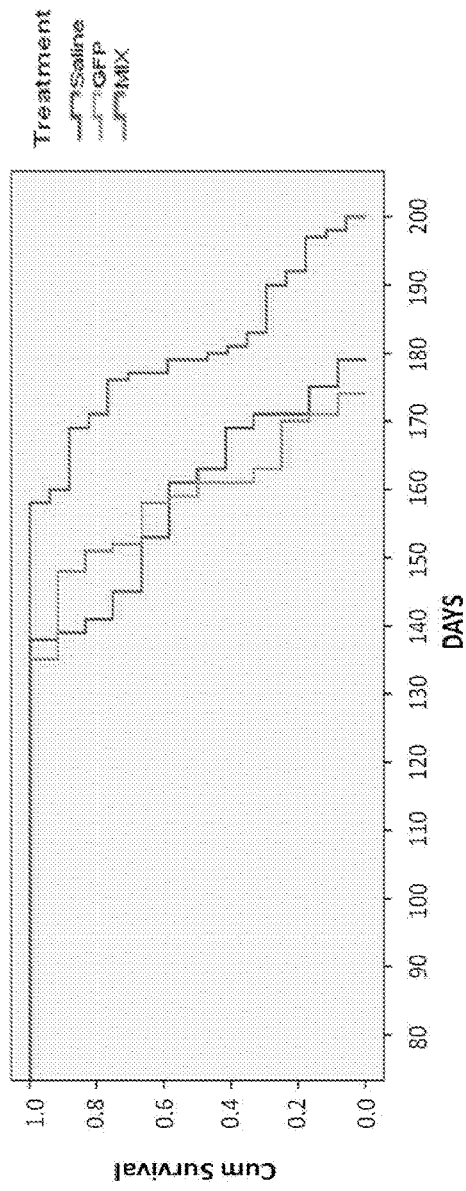
Figure 12F:
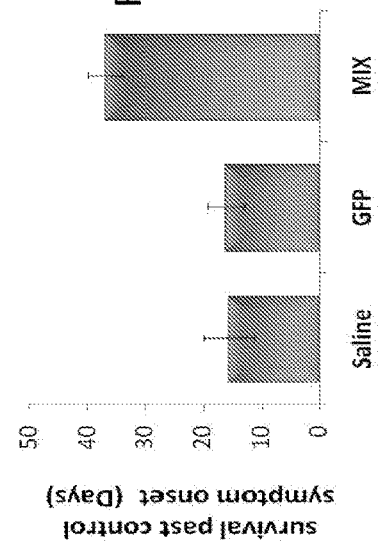
Figure 12E:
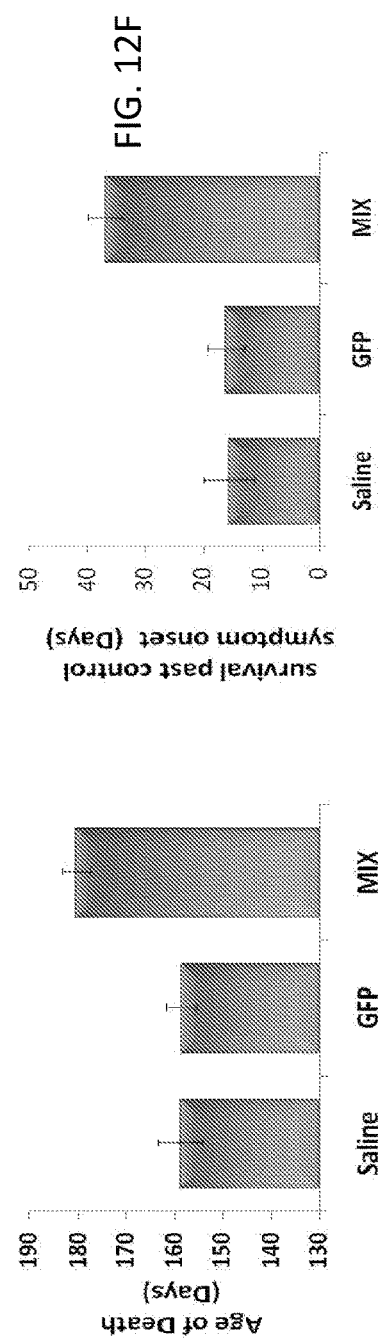

More specifically, on average, male mice treated with all three genes had a neurological score 2.25±0.28 points higher and weighed 6.05±0.33% more than their saline treated counterparts, as illustrated in FIGS. 6A and 6C. This treatment also succeeded in increasing the survival of the treated mice. The treatment significantly prolonged survival in male mice by 18.96±4.81 and 12.5±2.40 days compared to mice treated with saline or GFP respectively (FIGS. 12 A,B). This correlates with a 119.66% increased survival from the onset of symptoms in treated mice (compared to saline, FIG. 12C). In females, the survival was increased even further, with the treatment prolonging survival by 21.31±4.32 and 20.83±3.17 days compared to mice treated with saline or GFP respectively (FIGS. 12 D,E). This correlates with a 136.27% increased survival from the onset of symptoms in treated mice (compared to saline, FIG. 12F).

Figure 17:
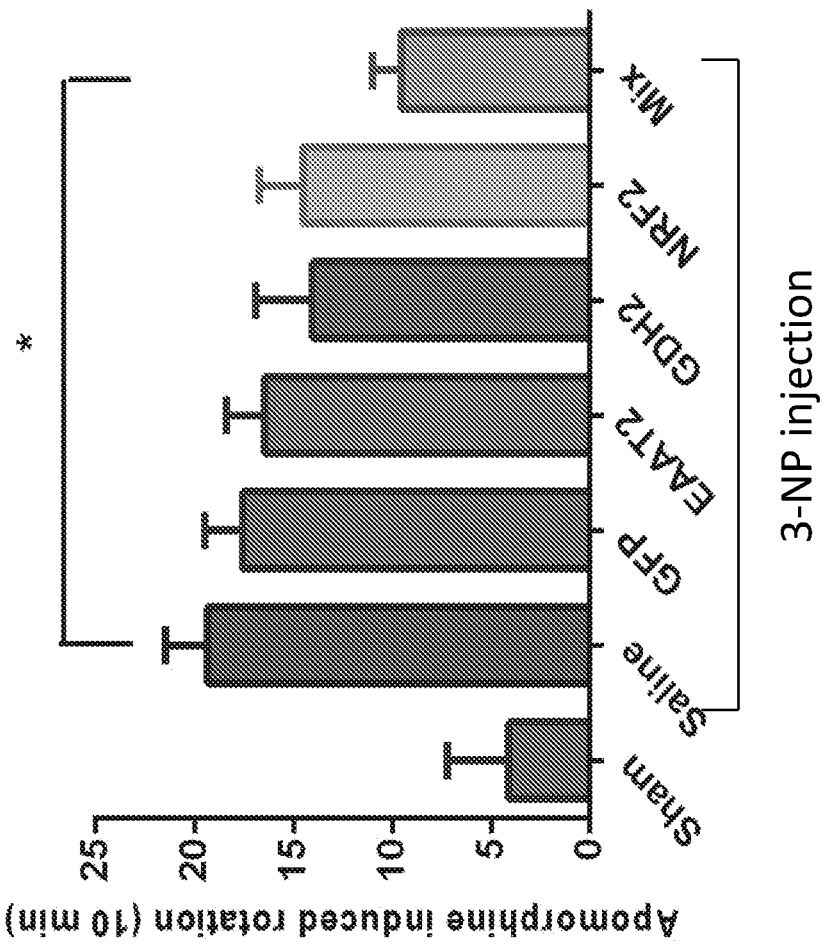
FIG. 17 is a graph illustrating the effect of EAAT2, NRF2 and GDH2 (MIX) on apomorphine-induced rotational behavior following 3-NP administration. Significant differences in the number of ipsilateral rotations were observed in treated mice (Mix) compared with control mice (Saline), indicating that after the mixed gene infusion there is a reduction in the levels of neurodegeneration of striatal cells.

In the MSA mouse model, the treatment effectively improved motor function (Cylinder test) following 3-NP administration (FIG. 18) and reduced the number of amphetamine induced rotations following 3-NP administration (FIG. 17).

Based on these encouraging results the present inventors believe that translation of this novel therapeutic approach could be a first step towards slowing the disease progression and alleviating the symptoms of patients suffering from neurodegenerative diseases such as ALS and MSA.

Thus, according to a first aspect of the present invention there is provided a method of treating a disease selected from the group consisting of emphysema, sepsis, septic shock, ischemic injury, cerebral ischemia, a neurodegenerative disorder, meningitis, encephalitis, hemorrhage, cerebral ischemia, heart ischemia and a cognitive deficit in a subject in need thereof comprising administering to the subject a therapeutically effective amount of a combination of at least two agents, wherein a first of the two agents is an antioxidant and a second of the two agents is a glutamatergic modulator, thereby treating the disease.

As used herein, the term "antioxidant" refers to a substance capable of reacting with and neutralizing free radicals. Examples of such substances include beta-carotene, selenium, coenzyme Q10 (ubiquinone), thiol, ascorbic acid, polyphenol, glutathione, catalase, superoxide dismutase, peroxidase, lutein, tocotrienols, soy isoflavones, S-adenosylmethionine, glutathione, N-acetylcysteine, vitamin E, vitamin C, and alpha-lipoic acid. Examples of foods containing useful levels of one or more antioxidants include but are not limited to *ginkgo biloba*, green tea, broccoli, citrus pulp, grape pomace, tomato pomace, carrot, spinach, and a wide variety of fruit and vegetable meals.

According to a particular embodiment, the antioxidant upregulates an activity and/or expression of Nrf2.

As used herein, the term "Nrf2" refers to the transcription factor that responds to oxidative stress that has a sequence at least 90%, 91%, 92%, 93%, 94%, 95%, 96%, 97%, 98%, 99%, 100% identical or homologous to the sequence as set forth in Uniprot No. 16236 or SEQ ID NO: 1, RefSeq mRNA NM_001145412 and/or RefSeq protein NP_001138884. An exemplary amino acid sequence of Nrf2 is set forth in SEQ ID NO: 1, which is encoded by the polynucleotide sequence as set forth in SEQ ID NO: 2.

Upregulators of activity and/or expression of Nrf2 include lipoic acid, tBHQ (Shih et al., J Biol Chem. 2005; 280(24): 22925-36; Shih et al., J Neurosci. 2005; 25:10321-10335), 3H-1,2-dithiole-3-thione (Burton et al., Neurotoxicology. 2006; 27:1094-100) and sulforaphane (Zhao et al., Stroke. 2007; 38(12):3280-6; Zhao et al., J Neurosci. 2007; 27(38): 10240-8). Other potential activators include NEPP compounds (Satoh et al., Proc Natl Acad Sci USA. 2006; 103(3):768-73), carnosic acid (Satoh et al., Neurochem. 2007; 104(4):1116-31) and triterpenoids.

Additional agents which upregulate Nrf-2 include, but are not limited to NAD(P)H quinone oxidoreductase 1 (Nqo1), Glutamate-cysteine ligase, catalytic (Gclc), UYglutamate-cysteine ligase, modifier (GCLM), Heme oxygenase-1 (HMOX1, HO-1), glutathione S-transferase (GST), UDP-lucuronosyltransferase (UGT) and Multidrug resistance-associated proteins (Mrps).

Another way of upregulating the activity or Nrf2 is by providing a polynucleotide that encodes the protein (e.g. gene therapy), as further described herein below.

Kelch-like ECH-associated protein 1 (Keap1) is a repressor of Nrf2 activation. Its mRNA sequence is set forth in NM_012289 and its protein sequence is set forth in NP_036421.

Accordingly, the present inventors contemplate use of an antioxidant which causes dissociation of Kelch-like ECH-associated protein 1 (Keap1) from Nrf2.

Examples of Keap1 repressors include oleane triterpenoid compounds such as Bardoxolone methyl.

According to still another embodiment, the antioxidant is an agent that downregulates an activity and/or expression of Keap1.

Polynucleotide agents which downregulate expression of Keap1 are described herein below.

The phrase "glutamatergic modulator" refers to an agent which affects the amount of glutamate in the cell. According to this aspect of the present invention, the glutamatergic modulator decreases the amount of glutamate in the cell.

Thus, the gluatmatergic modulator may act to reduce the synthesis of glutamate in the cell, increase the metabolism of glutamate in the cell or increase the rate of transport of glutamate out of the cell.

According to one embodiment, the glutamatergic modulator increases the amount and/or activity of a glutamate transporter. The transporter may belong to one of two classes of glutamate transporters, those that are dependent on an electrochemical gradient of sodium ions (the EAATs) and those that are not (VGLUTs and xCT).

Examples of glutamate transporters include, but are not limited to excitatory amino acid transporter 1 (EAAT1), EAAT2, and EAAT3.

EAAT1 may have an mRNA sequence at least 90%, at least 91%, at least 92%, at least 93%, at least 94%, at least 95%, at least 96%, at least 97%, at least 98%, at least 99% or 100% identical or homologous to the sequence as set forth in NM_001166695 and a protein sequence at least 90% at least 91%, at least 92%, at least 93%, at least 94%, at least 95%, at least 96%, at least 97%, at least 98%, at least 99% or 100% identical or homologous to the sequence as set forth in NP_001160167.

EAAT2 may have an mRNA sequence at least 90%, at least 91%, at least 92%, at least 93%, at least 94%, at least 95%, at least 96%, at least 97%, at least 98%, at least 99% or 100% identical or homologous to the sequence as set forth in NM_001195728 and a protein sequence at least 90%, at least 91%, at least 92%, at least 93%, at least 94%, at least 95%, at least 96%, at least 97%, at least 98%, at least 99% or 100% identical or homologous to the amino acid sequence as set forth in NP_ NP_001182657 or SEQ ID NO: 3.

An exemplary amino acid sequence of EAAT2 is set forth in SEQ ID NO: 3, which is encoded by the polynucleotide sequence as set forth in SEQ ID NO: 4.

EAAT3 may have an mRNA sequence at least 90%, at least 91%, at least 92%, at least 93%, at least 94%, at least 95%, at least 96%, at least 97%, at least 98%, at least 99% or 100% identical or homologous to the sequence as set forth in NM_004170 and a protein sequence at least 90%, at least 91%, at least 92%, at least 93%, at least 94%, at least 95%, at least 96%, at least 97%, at least 98%, at least 99% or 100% identical or homologous to the sequence as set forth in NP_004161.

The glutamatergic modulator may increase an expression and/or activity of least one glutamate modifying enzyme.

As used herein "a glutamate modifying enzyme" is an enzyme, which utilizes glutamate as a substrate and produces a glutamate reaction product. Numerous glutamate modifying enzymes are known in the art. For example, transaminases, which play a central role in amino acid metabolism and generally funnel alpha-amino groups from a variety of amino acids via the coupled conversion of glutamate into alpha-ketoglutarate or of alpha-ketoglutarate into glutamate.

Examples of transaminases include but are not limited to glutamate oxaloacetate transaminases, glutamate pyruvate transaminases, acetylomithine transaminases, ornithine-oxo-acid transaminases, succinyldiaminopimelate transaminases, 4-aminobutyrate transaminases, alanine transaminases (note: same as glutamate pyruvate transaminases, (s)-3-amino-2-methylpropionate transaminases, 4-hydroxyglutamate transaminases, diiodotyrosine transaminases, thyroid-hormone transaminases, tryptophan transaminases, diamine transaminases, cysteine transaminases, L-Lysine 6-transaminases, histidine transaminases, 2-aminoadipate transaminases, glycine transaminases, branched-chain-amino-acid transaminases, 5-aminovalerate transaminases, dihydroxyphenylalanine transaminases, tyrosine transaminases, phosphoserine transaminases, taurine transaminases, aromatic-amino-acid transaminases, aromatic-amino-acid-glyoxylate transaminases, leucine transaminases, 2-aminohexanoate transaminases, ornithine (lysine) transaminases, kynurenine-oxoglutarate transaminases, D-4-hydroxyphenylglycine transaminases, cysteine-conjugate transaminases, 2,5-diaminovalerate transaminases, histidinol-phosphate transaminases, diaminobutyrate-2-oxoglutarate transaminases, UDP-2-acetamido-4-amino-2,4,6-trideoxyglucose transaminases and aspartate transaminases (please note: same as glutamate oxaloacetate transaminases).

Another example of a glutamate modifying enzymes is a glutamate dehydrogenases, which generate ammonium ion from glutamate by oxidative deamination. Glutamate dehydrogenase has an EC number of 1.4.1.2. The glutamate dehydrogenase may be glutamate dehydrogenase 1 (NM_005271, P00367) or glutamate dehydrogenase 2 (NM_012084; P49448).

According to a particular embodiment, the glutamate dehydrogenase comprises an amino acid sequence at least 90%, 91%, 92%, 93%, 94%, 95%, 96%, 97%, 98%, 99%, 100% identical or homologous to the sequence as set forth in P49448 or SEQ ID NO: 5.

An exemplary amino acid sequence of glutamate dehydrogenase 2 is set forth in SEQ ID NO: 5, which is encoded by the polynucleotide sequence as set forth in SEQ ID NO: 6.

Other examples of glutamate modifying enzymes include but are not limited to decarboxylases such as glutamate decarboxylase; ligases such as glutamate-ethylamine ligase, glutamate-cysteine ligase; transferases such as glutamate N-acetyltransferase and N2-acetyl-L-ornithine, adenylyltransferase; aminomutases such as glutamate-1-semialdehyde 2,1-aminomutase and glutamate racemase [Glavas and Tanner (2001) Biochemistry 40(21):6199-204)].

The glutamatergic modulator according to this aspect of the present invention, can include one or more co-factors of glutamate modifying enzymes, which can accelerate activity of the latter (Vmax). These can be administered in order to enhance the rate of endogenous glutamate modifying enzymes or in conjunction with glutamate modifying enzymes (described hereinabove).

Co-factors of glutamate-modifying enzymes include but are not limited to oxaloacetate, pyruvate, NAD+, NADP+, 2-oxohexanedioic acid, 2-oxo-3-sulfopropionate, 2-oxo-3-sulfinopropionic acid, 2-oxo-3-phenylpropionic acid, 3-indole-2-oxopropionic acid, 3-(4-hydroxyphenyl)-2-oxopropionic acid, 4-methylsulfonyl-2-oxobutyric acid, 3-hydroxy-2-oxopropionic acid, 5-oxopentanoate, 6-oxohexanoate, glyoxalate, 4-oxobutanoate, .alpha.-ketoisocaproate, .alpha.-ketoisovalerate, .alpha.-keto-.beta.-methylvalerate, succinic semialdehyde-(-4-oxobutyrate), 3-oxoisobutanoate, pyridoxal phosphate, 5-oxopentanoate, 6-oxohexanoate and their artificially modified derivatives (e.g., esters).

It will be appreciated that the agent according to this aspect of the present invention may also include inhibitors of glutamate synthesizing enzymes (e.g., phosphate activated glutaminase). Numerous inhibitors of glutamate producing enzymes are known in the art. Examples include but are not limited gabapentin which has been shown to modulate the activity of branched chain aminotransferases [Taylor (1997) Rev. Neurol. 153(1):539-45] and aspirin at high doses (i.e., 4-6 g/day) a neuroprotective drug against glutamate excitotoxicity [Gomes (1998) Med. J. India 11:14-17]. Other inhibitors may be identified in the publicly available BRENDA, a comprehensive enzyme information system. Examples include but are not limited to, gamma-Acetylenic GABA, GABAculine, L-canaline, 2-amino-4-(aminooxy)-n-butanoic acid; 3-Chloro-4-aminobutanoate; 3-Phenyl-4-aminobutanoate; Isonicotinic hydrazide; (S)-3-Amino-2-methylpropanoate; Phenylhydrazine; 4-Fluorophenyl) alanine; Adipate, Azelaic acid, Caproate, 3-Methylglutarate, Dimethylglutarate, Diethylglutarate, Pimelate, 2-Oxoglutamate; 3-Methyl-2-benzothiazolone hydrazone hydrochloride; Phenylpyruvate, 4-Hydroxyphenylpyruvate, Prephenate, Indole pyruvate and their artificially modified derivatives (e.g., esters).

Polynucleotide inhibitors of enzymes involved in the synthesis of glutamate are further described herein below.

It will be appreciated that the present invention contemplates administering more than one glutamatergic modifier. Preferably, the combination is such that each of the agents in the combination of agents affects a different enzyme in the glutamate synthesis pathway. Thus, for example a particular combination contemplated by the present invention is an agent which upregulates expression of a glutamate transporter (EAA2) and an agent which upregulates expression of glutamate dehydrogenase.

Thus, according to another aspect of the present invention there is provided a method of treating a disease selected from the group consisting of emphysema, sepsis, septic shock, ischemic injury, cerebral ischemia, a neurodegenerative disorder, meningitis, encephalitis, hemorrhage, cerebral ischemia, heart ischemia and a cognitive deficit in a subject in need thereof comprising administering to the subject a therapeutically effective amount of a combination of at least three agents, wherein a first of the three agents upregulates an activity and/or expression of EAAT2, a second of the three agents upregulates an activity and/or expression of glutamate dehydrogenase and a third of the three agents upregulates an activity and/or expression of Nrf2, thereby treating the disease.

The agents which are used to treat the diseases described herein may be polynucleotide agents, protein agents, peptide agents, small molecule agents.

When two agents are used to treat the diseases described herein, they may be both polynucleotide agents, both protein agents, both peptide agents or both small molecule agents. Alternatively, one of the agents may belong to one class of agents (e.g. small molecule agents) and one of the agents may belong to another class of agents (e.g. polynucleotide agents).

When three agents are used to treat the diseases described herein, they may be each polynucleotide agents, each protein agents, each peptide agents or each small molecule agents. It will be appreciated that combinations of different classes of agents are also contemplated.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

Upregulation of an antioxidant and/or a glutamatergic modulator can be effected at the genomic level (i.e., activation of transcription via promoters, enhancers, regulatory elements), at the transcript level (i.e., correct splicing, polyadenylation, activation of translation) or at the protein level (i.e., post-translational modifications, interaction with substrates and the like).

Following is a list of agents capable of upregulating the expression level and/or activity of the active agents described herein (e.g. Nrf-2, EEAT2, and glutamate dehydrogenase).

An agent capable of upregulating expression of the above described agents may be an exogenous polynucleotide sequence designed and constructed to express at least a functional portion of the protein. Accordingly, the exogenous polynucleotide sequence may be a DNA or RNA sequence encoding the molecule, capable of anti-oxidant activity and/or glutamatergic modulations.

The phrase "functional portion" as used herein refers to part of the protein (i.e., a polypeptide) which exhibits functional properties of the protein (e.g. enzyme or Nrf2) such as binding to a substrate.

It will be appreciated that the polynucleotide may encode a naturally occurring glutamate modifying enzyme or an enzyme which has been modified to obtain improved features, such as higher affinity to glutamate than to a modified glutamate, stability under physiological conditions, solubility, enhanced enantioselectivity, increased thermostability and the like.

Another agent capable of upregulating expression of the above described agents may be a miRNA inhibitor.

Thus, in other embodiments of the invention, there are synthetic single stranded nucleic acids that are miRNA inhibitors. An miRNA inhibitor is typically between about 17 to 25 nucleotides in length and comprises a 5' to 3' sequence that is at least 90% complementary to the 5' to 3' sequence of a mature miRNA. In certain embodiments, an miRNA inhibitor molecule is 17, 18, 19, 20, 21, 22, 23, 24, or 25 nucleotides in length, or any range derivable therein. Moreover, an miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA.

The miRNA inhibitors may be administered to the subject (or contacted with cells) using transient transfection techniques. miRNA inhibitors are commercially available from Companies such as Applied Biosystems.

Alternatively, the miRNA inhibitors may be part of an expression vector, as described herein above. In this case, cells may be transiently or stably transfected with the vector.

To express polynucleotides in mammalian cells, the polynucleotide sequence (e.g. one encoding the protein or miRNA inhibitor) is preferably ligated into a nucleic acid construct suitable for mammalian cell expression. Such a nucleic acid construct includes a promoter sequence for directing transcription of the polynucleotide sequence in the cell in a constitutive or inducible manner.

It will be appreciated that the nucleic acid construct of some embodiments of the invention can also utilize homologues which exhibit the desired activity (i.e., antioxidant activity and/or glutamatergic modulation. Such homologues can be, for example, at least 90%, at least 91%, at least 92%, at least 93%, at least 94%, at least 95%, at least 96%, at least 97%, at least 98%, at least 99% or 100% identical to the naturally occurring sequences as provided herein, determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for the tetracycline-inducible promoter (Zabala M, et al., Cancer Res. 2004, 64(8): 2799-804).

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

Thus, for example the present invention contemplates a single expression vector which encodes 2 or even 3 of the agents used to treat the diseases described herein.

It will be appreciated that the individual elements comprised in the expression vector can be arranged in a variety of configurations. For example, enhancer elements, promoters and the like, and even the polynucleotide sequences the above described proteins can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A⁺, pMT010/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of the above described proteins since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

The present invention contemplates viral particles which express at least 2 or even 3 of the protein agents described herein. For example, according to one embodiment, there is provided a viral particle (e.g. a lentiviral particle) which are genetically engineered to express EAAT2, NRF2 and GDH2.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

It will be appreciated that the nucleic acid construct can be administered to the individual employing any suitable mode of administration, described hereinbelow (i.e. in vivo gene therapy). Alternatively, the nucleic acid construct can be introduced into a suitable cell using an appropriate gene delivery vehicle/method (transfection, transduction, etc.) and an appropriate expression system, as further described herein below. The modified cells are subsequently expanded in culture and returned to the individual (i.e. ex vivo gene therapy).

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the protein of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the protein and the heterologous protein, the protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of E. coli expression vectors [Studier et al. (1990) Methods in Enzymol. 185:60-89].

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described herein below can also be used by some embodiments of the invention.

Recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

As mentioned herein above the present invention also contemplates providing agents which down-regulate particular proteins—e.g. keap-1 or glutamate synthase.

Downregulation of such proteins can be effected on the genomic and/or the transcript level using a variety of molecules which interfere with transcription and/or translation [e.g., RNA silencing agents (e.g., antisense, siRNA, shRNA, micro-RNA), Ribozyme and DNAzyme], or on the protein level using e.g., antagonists, enzymes that cleave the polypeptide and the like.

One example, of an agent capable of downregulating a protein is an antibody or antibody fragment capable of specifically binding to that protein. Preferably, the antibody specifically binds at least one epitope of the protein. As used herein, the term "epitope" refers to any antigenic determinant on an antigen to which the paratope of an antibody binds.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Downregulation of proteins can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., keap-1) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level.

Second, potential target sites are compared to an appropriate genomic database (e.g., human, mouse, rat etc.) using any sequence alignment software, such as the BLAST software available from the NCBI server. Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348, 185, the contents of which are expressly incorporated herein by reference. The cell-penetrating peptides of some embodiments of the invention preferably include, but are not limited to, penetratin, transportan, plsl, TAT(48-60), pVEC, MTS, and MAP.

According to another embodiment the RNA silencing agent may be a miRNA or a miRNA mimic.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

It will be appreciated from the description provided herein above, that contacting cells with a miRNA may be affected in a number of ways:

1. Transiently transfecting cells with the mature double stranded miRNA;
2. Stably, or transiently transfecting the cells with an expression vector which encodes the mature miRNA.
3. Stably, or transiently transfecting the cells with an expression vector which encodes the pre-miRNA. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 5-10 or variants thereof.
4. Stably, or transiently transfecting the cells with an expression vector which encodes the pri-miRNA The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof.

Preparation of miRNAs mimics can be effected by chemical synthesis methods or by recombinant methods.

Additional agents that may down-regulate proteins include DNAzymes, ribozymes, antisense oligonucleotides, triplex forming oligonucleotides (TFOs), inhibitory peptides and non-functional analogues.

As mentioned herein above, protein or polynucleotide agents may also be administered by providing protein-or polynucleotide-expres sing cells into the individual. The cells may naturally express the proteins or may be genetically modified to express the proteins.

Such protein-expressing cells can be any suitable cells, such as kidney, bone marrow, keratinocyte and lymphocyte cells which are derived from the individuals and are transfected ex vivo with an expression vector containing the polynucleotide designed to express the proteins as described hereinabove. According to a particular embodiment, the cells are stem cells such as embryonic stem cells, mesenchymal stem cells or induced pluripotent stem cells.

Administration of the protein-expressing cells of some embodiments of the invention can be effected using any suitable route such as intravenous, intra peritoneal, intra kidney, intra gastrointestinal track, subcutaneous, transcutaneous, intramuscular, intracutaneous, intrathecal, epidural and rectal. According to presently preferred embodiments, the protein-expressing cells of some embodiments of the invention are introduced to the individual using intravenous, intra kidney, intra gastrointestinal track and/or intra peritoneal administrations.

Protein-expressing cells of some embodiments of the invention can be derived from either autologous sources such as self bone marrow cells or from allogeneic sources such as bone marrow or other cells derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnam-ylidene-acetylated poly(allylamine). Biotechnol Bioeng. 2000, 70: 479-83, Chang™ and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylide-neacetate). J Microencapsul. 2000, 17: 245-51.

For example, microcapsules are prepared by complexing modified collagen with a ter-polymer shell of 2-hydroxy-ethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002; 13: 783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

An agent capable of upregulating one of the proteins described above may also be any compound which is capable of increasing the transcription and/or translation of an endogenous DNA or mRNA encoding that protein and thus increasing its endogenous activity.

An agent capable of upregulating a protein described herein above may also be an exogenous polypeptide including at least a functional portion (as described hereinabove) of the protein.

Any and all modifications which can result in increased genetic presence, protein expression, mRNA expression and/or function which yield a synergy between anti-oxidative function and improved glutamate balance are envisioned. For example viral delivery of such genes, chemical activation of these genes, pharmaceutically increased protein function, etc.

As mentioned, the agents provided to treat the diseases described herein are typically a combination of at least two agents.

Thus, according to another aspect of the present invention there is provided an article of manufacture comprising at least two agents, wherein a first of the at least two agents upregulates an activity and/or expression of Nrf2 and a second of the at least two agents is a glutamatergic modulator.

According to still another aspect of the present invention there is provide an article of manufacture comprising at least three agents, wherein a first of the three agents upregulates an activity and/or expression of EAAT2, a second of the three agents upregulates an activity and/or expression of glutamate dehydrogenase and a third of the three agents is an antioxidant.

Agents that upregulate an activity and/or expression of Nrf2 have been described herein above.

Agents that upregulate an activity and/or expression of EAAT2 have been described herein above.

Agents that upregulate an activity and/or expression of glutamate dehydrogenase have been described herein above.

Antioxidant agents have been described herein above.

At least two of the agents can be combined in a single composition and administered to the subject. Alternatively, the agents can be formulated as single compositions and provided individually.

For polynucleotide agents which encode proteins of the present invention, it will be appreciated that a single nucleic acid construct may be engineered to express at least two proteins or even three proteins. Also, viruses may be engineered to express one, two, three or more of the proteins described herein above.

The agents of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antioxidant agents and the glutamate modulating agents accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences", Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections. Another contemplated route of administration includes the intra-cisternal route of delivery which includes delivery of the agents into the subjects CSF, the agents are then carried with the CSF allowing them to reach cells dispersed throughout the brain and spinal cord. To increase the penetration potential of the agents, intra-cisternal injections may accompanied by pre-treatment with agents that increase the penetration of the blood brain barrier such as mannitol.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (antioxidant agents and the glutamate modulating agents) effective to prevent, alleviate or ameliorate symptoms of a disorder (e.g., ALS) or prolong the survival of the subject being treated.

Determination of a therapeutically effective amount is well within the capability of those skilled in the art, especially in light of the detailed disclosure provided herein.

The present inventors contemplate that a dose of infectious viral particles (e.g. which are manipulated to express each of EAAT2, NRF2 and GDH2) is between $10 \times 10^8$ infectious viral particles—$10 \times 10^9$ infectious viral particles (e.g. $50 \times 10^8$ infectious viral particles—$100 \times 10^8$ infectious viral particles.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans. A suitable animal model to ascertain the effect of the compositions are transgenic SOD1 (superoxide dismutase 1) mice. These mice express a G93A mutant form of human SOD1 and exhibit a phenotype similar to amyotrophic lateral sclerosis (ALS) in humans, an age-related rapidly progressive decline of motor functions accompanied by degenerative changes of motoneurons within the spinal cord, brain stem and neocortex. In this ALS mice model, motor neurons loss starts at a very young and asymptomatic age; the first symptoms such as reduced electrical nerve conductivity begin at the age of 40 days postnatal. The first signs of motor deterioration become visible around age of 70-80 days when the mouse's hind limbs start to tremble. The symptoms slowly progress, motor function begins to deteriorate at 120 days and full visible symptoms appear at the age of 140 days. From the onset of symptoms the disease progresses very quickly and the mice die at an average age of 155 days.

A suitable animal model which may be used to ascertain the effects of the agents described herein is a mouse following 3-NP striatal injection for the treatment of MSA.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide brain or muscle levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The kit may comprise each of the active agents packaged individually, a combination of at least two of the agents packaged in the same packaging (or even the same formulation), a combination of three of the agents packaged in the same packaging (or even the same formulation). The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Exemplary conditions that may be treated using the agents of the present invention include but are not limited to emphysema, sepsis, septic shock, ischemic injury, cerebral ischemia, a CNS disease, meningitis, encephalitis, hemorrhage, cerebral ischemia, heart ischemia and a cognitive deficit.

Representative examples of CNS diseases or disorders that can be beneficially treated with the cells described herein include, but are not limited to, a pain disorder, a motion disorder, a dissociative disorder, a mood disorder, an affective disorder, a neurodegenerative disease or disorder and a convulsive disorder.

More specific examples of such conditions include, but are not limited to, Parkinson's, Amyotrophic Lateral Sclerosis (ALS), Multiple System Atrophy (MSA), Multiple Sclerosis, Huntingdon's disease, autoimmune encephalomyelitis, diabetic neuropathy, glaucatomus neuropathy, macular degeneration, action tremors and tardive dyskinesia, panic, anxiety, depression, alcoholism, insomnia, manic behavior, Alzheimer's and epilepsy.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton &

Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Reduced Glutamate Uptake Capacities in SOD1 G93A Astrocytes

Astrocyte enriched primary cultures were generated from postnatal Days 1-3 wild-type and SOD1 G93A mice. The use of appropriate culture medium combined with a vigorous mechanical dissociation step promoted the enrichment of astrocytes and the elimination of microglia cells from the culture. Astrocyte enriched cultures were found to contain less than 4% microglia cells. In order to evaluate the glutamate uptake capacities of SOD1 G93A astrocytes, [$^3$H] D-aspartate-based saturation kinetics was studied and glutamate uptake assays were performed. Both assays utilized [$^3$H] D-aspartate as it is a commonly used nonmetabolized transportable glutamate analog which does not interact with glutamate receptors.

Results

Unactivated astrocytes derived from SOD1 G93A mice demonstrated a significantly lower maximal velocity (Vmax) of substrate uptake compared with their wild-type counterparts (Vmax wild-type: 6.45±0.09, SOD1 G93A: 3.51±0.08 nmol/min/mg, $P<0.01$, FIG. 1A). Glutamate transporter activity was considerably reduced in the absence of Na$^+$ and in the presence of the glutamate uptake inhibitor t-PDC (wild-type Na$^+$: 97.50±1.04%, t-PDC: 99.03±0.30%. SOD1 G93A Na$^+$ 96.60±1.04%, t-PDC: 98.52±0.39% reduction in substrate uptake. $P<0.001$, FIG. 1B). Astrocyte activation occurs in response to central nervous system insult and environmental stress. The present inventors next sought to evaluate whether such stress effects the astrocytic ability to take up glutamate. To this end they selected three treatments, the bacterial endotoxin LPS, which is known to cause acute astroglial and microglial activation, the G5-supplement a cocktail of growth factors designed to specifically activate astrocytes in a manner resembling mature type-II astrocytes (Michler-Stuke et al., 1984; Vermeiren et al., 2005). The third activator selected was the b-lactam antibiotic ceftriaxone (CEF), which specifically affects the astrocytic glutamatergic pathway. Activation of wild type astrocytes with G5, LPS, or CEF induced a robust increase in substrate uptake (G5: 153.83±11.30%, LPS: 175.30±20.51% and CEF 200.20±16.67% of unactivated astrocytes, $P<0.05$, FIG. 1C). However, not only do unactivated SOD1 G93A astrocytes take up substrate less efficiently (73.31±7.95% of wild-type astrocytes, $P<0.05$), but unlike their wild-type counterparts, in response to activation they show no further increase in substrate uptake (FIG. 1C).

Example 2

Generation and Evaluation of Lentiviral Constructs Engineered to Harbor the Genes: EAAT2, NRF2 and GDH2

Materials and Methods
Generation of Lentiviral Vectors
Four lentiviral vectors were constructed using ViraPower™ Promoterless Lentiviral Gateway® Kit (Invitrogen, Carlsbad, Calif., USA) according to the manufacturer's protocol:
pLenti6.3-CMV-EAAT2,
pLenti6.3-CMV-NRF2,
pLenti6.3-CMV-GDH2,
pLenti6.3-CMV-AcGFP2 (control).
The following vectors were used as set forth in Table 1 herein below:

TABLE 1

| Vector name | Manufacturer | Catalog# |
|---|---|---|
| pCR ®8/GW/TOPO ® | Invitrogen | K2500-20 |
| pLenti6/R4R2/V5-DEST | Invitrogen | Part of kit K5910-00 |
| pENTER-5'-CMV | Invitrogen | Custom ordered |
| pENTER-EAAT2 | ImaGenes | IOH42832 |
| pENTER-NRF2 | ImaGenes | IOH14493 |
| pENTER-GDH2 | ImaGenes | IOH27063 |
| pENTER-AcGFP | Invitrogen | Custom ordered |

The pENTER-Gene plasmid, pENTER-5'-CMV promoter plasmid and the pLenti-DEST destination plasmid were recombined using the LR Clonase II plus enzyme. This enzyme displaced the fragments flagged by the recombination sequences to produce the final pLenti6.3-CMV-GENE construct. The pLenti6.3 vectors also contain the Blasticidin resistance marker to select the cells expressing the vector.

Production of Lentiviral Particles: Viral particles containing the constructed vectors were produced by transducing 293T producer cell line and using the ViraPower™ Lentiviral Expression System (Invitrogen).

The lentiviral titer was determined using the Lenti-X p24 Rapid Titer Kit.

Transduction of Astrocytes with Lentiviral Vectors: The produced lentiviral particles containing EAAT2, NRF2, GDH2 or GFP were transduced into cortical astrocyte cultures derived from WT or SOD1 G93A mice. Transcription and translation of the genes were confirmed by real-time quantitative reverse transcription PCR and western blot analysis correspondingly. The transgene function in transduced astrocytes was evaluated by measuring the amount and function of NRF2 protein in the cell nucleus using the Active motif Nuclear Extract Kit and TransAM NRF2 activity kit. To evaluate whether the transduction of astrocytes with EAAT2 increased the function of the EAAT2 protein, the glutamate uptake was assessed using the [$^3$H]

D-aspartate assay. Cellular viability was assessed using the alamarBlue® assay (Invitrogen).

Results

The present inventors first determined the level of expression of the genes of interest and the functional state of the corresponding proteins in transduced cells. Following transduction of primary astrocytic cultures with EAAT2, NRF2, and GDH2, the total RNA and protein were extracted and the gene expression levels were determined by qRT-PCR.

Immunohistochemistry was used to evaluate the expression levels of the transfected genes in astrocytes. A substantial increase in the expression levels of the three genes was observed as compared to control (by expression of GFP). GFP levels were only detectable in cells infected with GFP viruses (FIGS. 2A, B).

The cellular viability compromised by the transduction procedure may affect the astrocytes' neuroprotective capacity. Therefore, the cellular viability of transduced and non-transduced astrocytes was assessed using alamarBlue® test. It was found that the transduction of astrocytes with EAAT2, NRF2, GDH2, GFP or their combination did not hinder their viability (FIG. 2C).

Transfection of SOD1 G93A astrocytes with lentiviral vectors encoding for EAAT2, GDH2 and NRF2 increased the astrocytic mRNA expression levels of each transgene respectively (FIG. 2D, F, H).

As the next step the functional state of the genes of interest were evaluated.

To test the functional state of EAAT2, the uptake of radiolabeled aspartate ([$^3$H]D-aspartate—the non-metabolized analog of L-glutamate—was measured. The transduction with lentiviruses containing EAAT2 significantly increased the rate of glutamate uptake, while the transduction of astrocytes with GFP had no effect on glutamate uptake (FIG. 2E). Next, the enzyme activity of GDH2 was evaluated (FIG. 2G). The gene of luciferase controlled by a promoter containing the anti-oxidant response element sequence (ARE) recognized by NRF2 was used to test the functional state of NRF2. The results demonstrated that the transduction of astrocytes with NRF2 significantly increases the GFP gene did not alter the luciferase luminescence (FIG. 2I). Transfection with lentiviral vectors encoding for NRF2 also increased the mRNA expression levels of two NRF2 downstream genes; GCLM and NQO1 (FIG. 2J, K).

Expression of the Genes EAAT2, NRF2 and GDH2 in SOD1 G93A Astrocytes Synergistically Increases their Neuroprotective Capacities To evaluate the effect of EAAT2, NRF2 and GDH2 overexpression on neuroprotective properties of SOD1 G93A astrocytes, the present inventors implemented an assay where survival rate of motor neuron like cells (NSC-34) was determined under conditions simulating excito-oxidative stress.

Figure 3A:
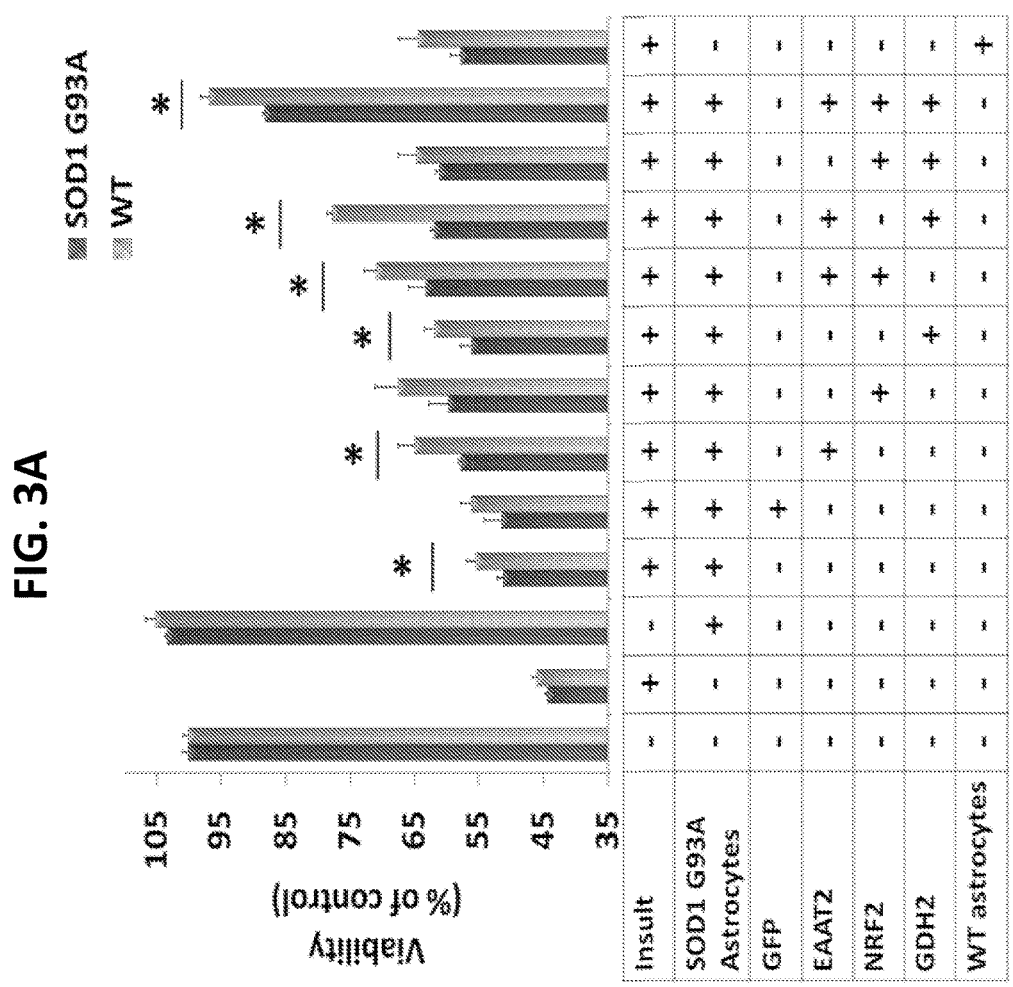
FIGS. 3A-B illustrate the neuroprotective effect of astrocytes transduced with different combinations of the EAAT2, NRF2 and GDH2 genes. (A) Transduced astrocytes were co-cultured with NSC-34 cells overexpressing SOD1 G93A or WT SOD1 and subsequently challenged with excito-oxidative insult (3.5 mM Glutamate combined with 17.5 nM H$_2$O$_2$) for 16 hours. Following the insult, the neuronal viability was assessed. Two data series refer to NSC-34 cells overexpressing SOD1 G93A or WT SOD1.

The most neuroprotective effect was achieved by transduction of the astrocytes with all three genes simultaneously, with the neuronal survival reaching approximately 90% of unchallenged control (FIG. 3A).

Figure 3B:
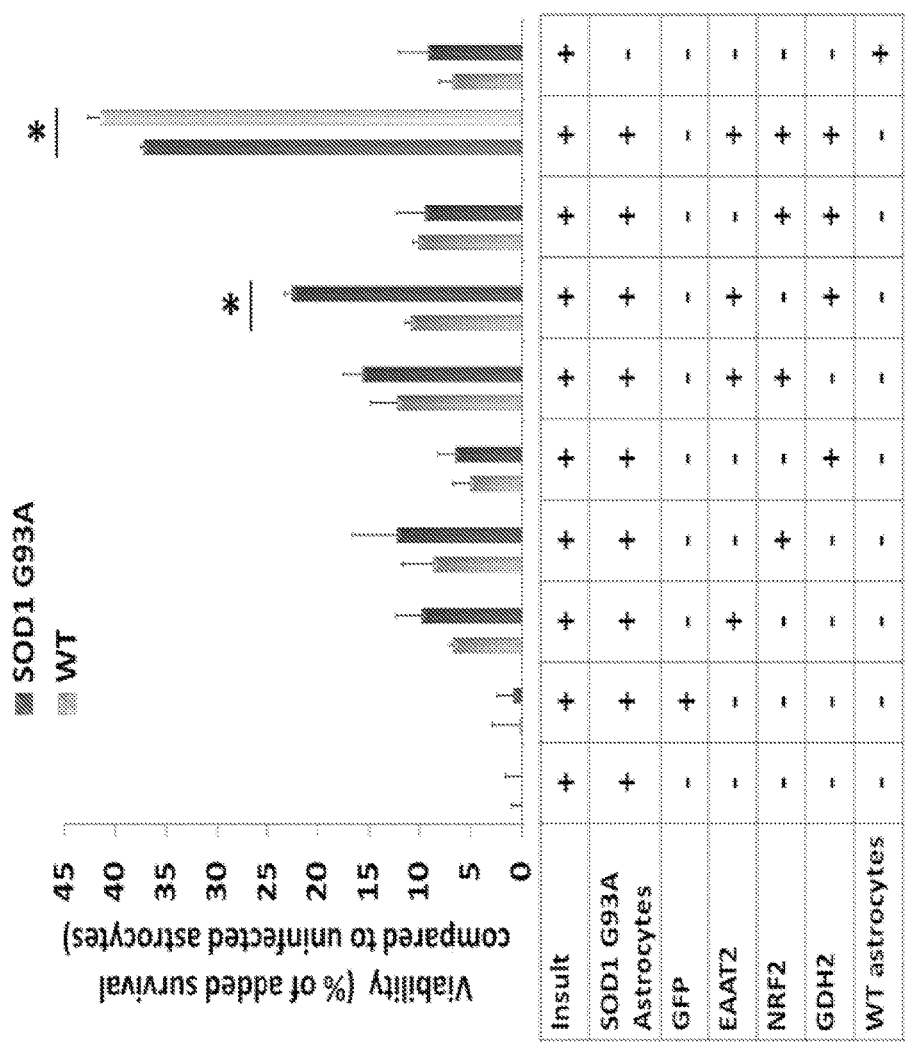

The neuroprotection provided by the differently transduced astrocytes was very similar when they were protecting either WT or mutant SOD1 overexpressing astrocytes, with SOD1 G93A overexpressing NSC-34 cells being slightly more sensitive to the excito-oxidative stress (FIG. 3B). These experiments established the dramatic synergistic relationship between overexpression of EAAT2, NRF2 and GDH2. The increase in neuroprotection exerted by astrocytes transduced with all three genes far exceeded the sum of that exerted by each individual gene, as well as that achieved by any partial combination between the three genes.

Figure 4:
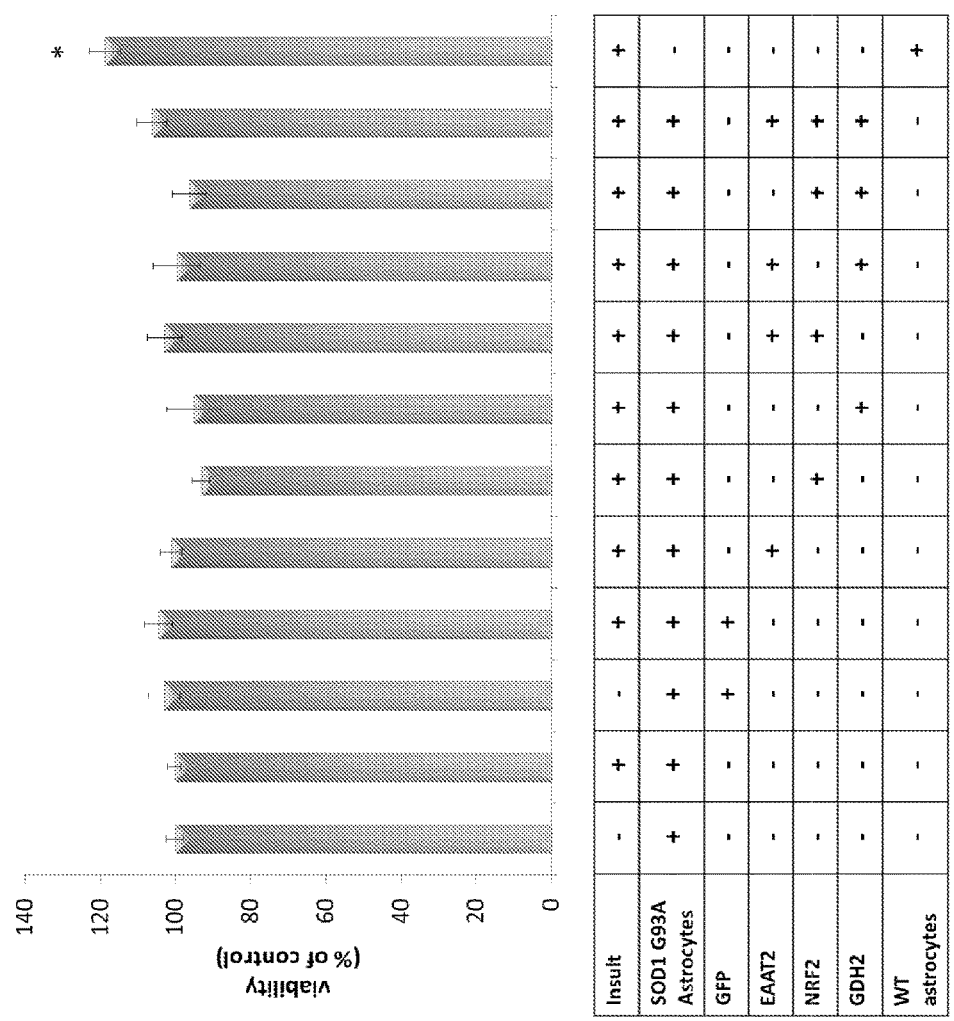
FIG. 4 illustrates that astrocytic viability is not affected by transduction or excito-oxidative stress. The viability of WT or SOD1 G93A astrocytes in the presence of excito-oxidative insult (3.5 mM glutamate combined with 17.5 mM H2O2), in response to the transduction procedure or a combination of the two.*p<0.05 compared to control. Error bars represent standard error.

Transduction of the astrocytes with the viral vectors had no effect on the astrocytic viability, nor did exposure to the excito-oxidative insult in any of the groups evaluated. The only group that showed slightly elevated astrocytic viability following the excito-oxidative insult was that of astrocytes derived from WT mice compared to the rest of the groups that were derived from SOD1 G93A mice (FIG. 4).

Example 3

Therapeutic Effect of Gene Therapy with EAAT2, NRF2 and GDH2 in a Mouse Model of ALS The objectives of the conducted in vivo studies were to evaluate the possible neuroprotective effect of the product by assessing behavioral and survival parameters in SOD1 G93A mice treated with the selected therapeutic combination of lentiviruses injected into the cerebrospinal fluid and hindlimb muscles. The present inventors also demonstrated the dispersion of the vectors through the spinal cord and incorporation of the viruses into the cellular DNA with expression of the viral marker BSD, 60 days following the treatment. In addition, the safety of the product was assessed by daily visual observation of the treated vs. control animals for any adverse events related to the treatment.

Experimental Design, as Depicted in FIG. 5

A colony of SOD1 G93A mice was established. When SOD1 mice became weak, food pellets were supplied inside the cage. Newborn litters were selected randomly for inclusion in control or treatment groups. The experimental design maintained a stud-mate distribution into the control or treatment groups. All experiments were performed by a blinded observer. At the age of 65 days, SOD1 G93A mice received either (1) lentiviruses carrying GFP, (2) one of the three genes, (3) a mixture of lentiviruses carrying each of EAAT2, NRF2 and GDH2, or (4) a non-viral saline (control). All mice were injected both intra-cisternaly and intramuscularly into the gastrocnemius muscles of both hind limbs. Mice received a total viral load of $1 \times 10^8$ infectious viral particles; half of the viral load was administered intra cisternaly and a quarter into each hind limb. Unless otherwise specified, a minimum of 12 animals per group per gender was maintained. Selected mice were sacrificed; immunohistochemistry was performed on spinal cord samples.

Neurological Score Evaluation by Ladder Testing of SOD1 Mice: To evaluate the animals overall neurological state, the present inventors performed a neurological scoring based on the ladder test, which is an extension of the hanger test. The ladder is placed at a 45-degree angle; after a brief training period, when placed on the ladder healthy mice quickly and efficiently climb up the ladder. As the disease progresses, the animals' ability to climb is hindered beginning with legs tremor and developing until the mice cannot climb the ladder at all. From the age of 90 days, the mice were evaluated for their neurological score twice weekly by a blinded observer. The mice were scored based on their performance on the ladder test with a score of 12 representing completely healthy mice and 0 correlating with the disease end stage.

Weight Measurement of SOD1 Mice: From the age of 40 days the animals were weighed weekly. The animal's weight at the time of death was recorded and used as the animal's terminal weight.

Hindlimb Reflex Measurement of SOD1 Mice: When lifted by their tails, healthy mice reflexively extend their legs backwards to improve their balance. As the disease progresses, SOD1 G93A ALS mice begin to lose their ability to extend their legs and this reflexive extension is gradually lost. From the age of 90 days, the mice were evaluated weekly for their hind leg reflexes by a blinded observer. Each leg was given a score of 0 to 100 (100 being fully extended leg and 0 no extension reflex observed). As the disease progresses bilaterally but not symmetrically, the animals' score was the combined score given to each leg.

Motor Function Measurement by Rotarod of SOD1 Mice

Adult wild-type mice are able to remain balanced on a rod rotating at 12.5 rpm for up to 4 min, following a brief training period. As SOD1 mice weaken, however, they lose this balancing ability and fall off the rod after progressively shorter periods of time. The ability of mice to perform this task was analyzed. All subjects were tested on a weekly basis starting at 90 days of age after three sessions of training.

Symptom Onset Evaluation of SOD1 Mice

The clinical condition of the mice was monitored daily starting at 40 days. The onset of clinical signs was scored following the animal's weight loss. The age of clinical onset was determined by the age (in days) at which the mice loss 5% of their body weight (compared to peak weight).

Survival evaluation of SOD1 Mice: The clinical condition of the mice was monitored daily starting at 40 days. The loss of righting reflex determined the end stage of the disease. The mice were sacrificed if they could not right themselves within 30 seconds when placed on either side on a flat surface. The age (in days) at which the mice were sacrificed represented the age of death and the extent of survival in accordance with currently accepted practices.

Safety Assessment: The animals were visually observed for treatment-related adverse events daily until the completion of the study.

Results

The mice were divided into 12 groups; each group was treated with either saline (male n=6, female n=5), GFP (male n=5, female n=8), EAAT2 (male n=7, female n=8), NRF2 (male n=4, female n=7), GDH2 (male n=4, female n=5) or a mixture of all three genes (MIX, male n=6, female n=9). The treatment was performed at the age of 65 days; the transgene expression slowly built up for approximately 10-15 days (FIG. 5). All mice were injected both intra-cisternaly and intra-muscularly. The neurological score and weight of the male and female groups was recorded at the age of 17 weeks and 18 weeks respectively.

The results demonstrated that the treatment with each of the individual genes separately was not sufficient to provide a therapeutic effect. However, treatment with all three genes combined had the ability to preserve the animals' neurological score and weight. On average, male mice treated with all three genes had a neurological score 2.25±0.28 points higher and weighed 6.05±0.33% more than their saline treated counterparts (FIGS. 6 A, C). Whereas female mice, treatment with all three genes had a neurological score 1.5±0.26 points higher than their saline treated counterparts (FIG. 6B). However, as at this age female mice have not yet started the phase of accelerated weight loss, the weight of treated females was not significantly different than their saline treated counterparts (at this age only a trend towards weight preservation was observed, FIG. 6D).

The synergistic relationship demonstrated in this result is strengthened even further by this particular experimental design in which the mixed treatment group that received all three genes was treated with a total viral amount equivalent to that given for each individual gene, leading to a situation in which this group only received a third of the amount of each gene given to the individual gene groups.

Taken together these results suggest a strong therapeutic potential of combined treatment with lentiviruses genetically engineered to express the genes; EAAT2, NRF2 and GDH2.

Figure 7B:
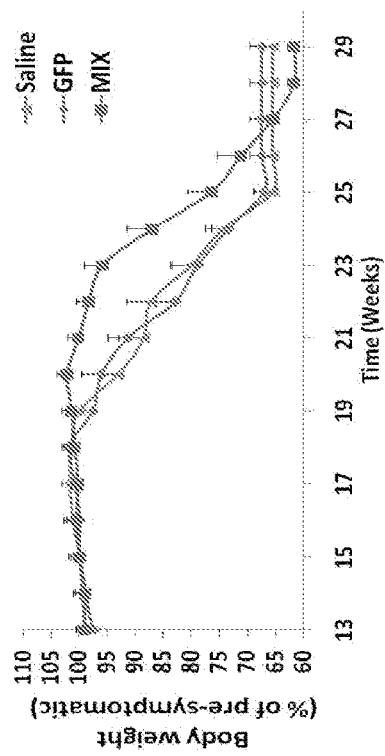
FIGS. 7A-B are graphs illustrating that treatment with EAAT2, NRF2 and GDH2 containing lentiviruses preserves body weight in SOD1 G93A ALS mice. The mice were injected with saline, lentiviruses containing GFP or a mixture of three types of lentiviruses each containing one of the three genes; EAAT2, NRF2 or GDH2 (MIX). Male (A) and female (B) body weight loss during disease progression (for MIX, P<0.001 as determined by two way ANOVA for repeated measures, 12<n>17 animals per group per gender).
Figure 7A:
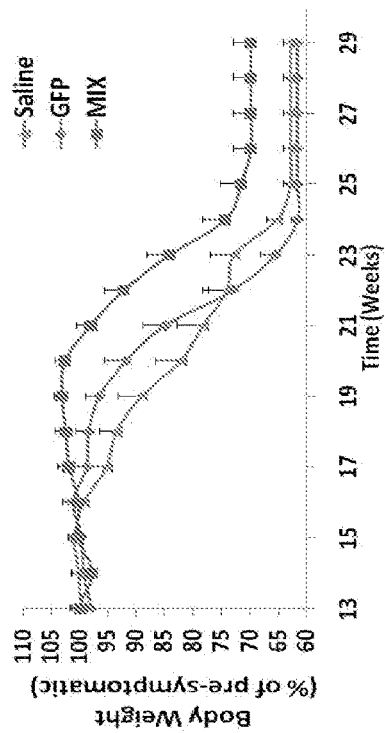

A treatment's influence on the animal's body weight is considered to be one of the best predictors of clinical success in the pre-clinical stage of any ALS treatment. Mice treated with saline or GFP lost 15% of their body weight at the age of 20 and 21 weeks in males respectively and 22 weeks in both female groups. The treatment was able to significantly delay the loss of body weight in both male and female mice reaching the same level of body weight loss at the age of 23 and 24 weeks, respectively (FIG. 7).

Figure 8B:
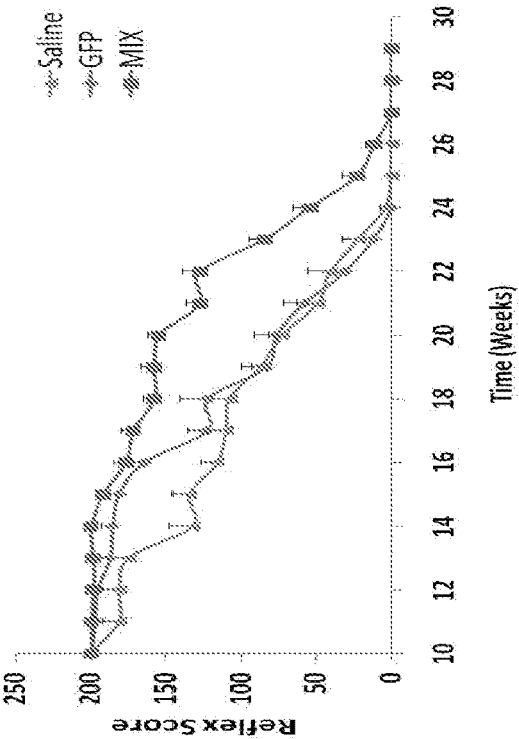
FIGS. 8A-B are graphs illustrating that treatment with EAAT2, NRF2 and GDH2 containing lentiviruses reduces the loss of hindlimb reflexes in SOD1 G93A ALS mice. The mice were injected with saline, lentiviruses containing GFP or a mixture of three types of lentiviruses each containing one of the three genes; EAAT2, NRF2 or GDH2 (MIX). Male (A) and female (B) hindlimbreflex loss during disease progression (for MIX, P<0.001 as determined by two way ANOVA for repeated measures. 12<n>17 animals per group per gender).
Figure 8A:
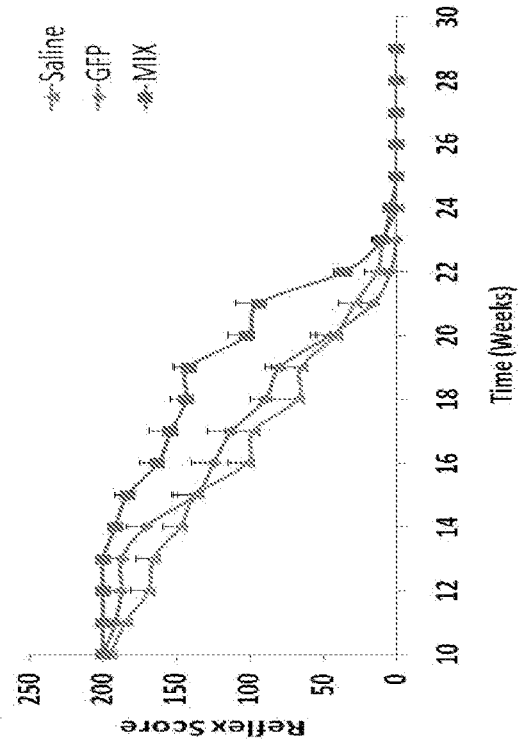

When healthy mice are lifted by their tail, they reflexively extend their legs backwards to improve their balance. As the disease progresses their ability to extend their legs decreases until they can no longer extend them at all. Mice treated with saline or GFP lost 50% of their hindlimb reflex between the ages of 17 to 18 weeks in males, and 18-19 weeks in females. The treatment was able to significantly delay the loss of hindlimb reflex in both male and female mice reaching the 50% loss of reflex between the ages of 20 and 21 weeks for males and 22 to 23 weeks in females (FIG. 8).

Figure 9A:
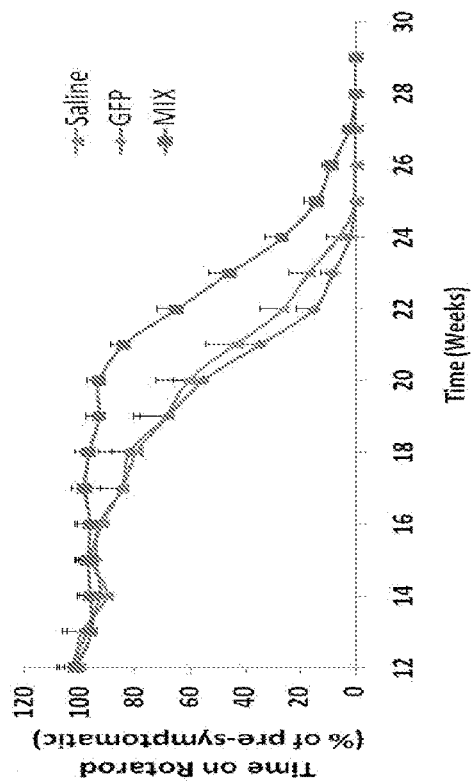
FIGS. 9A-B are graphs illustrating that treatment with EAAT2, NRF2 and GDH2 containing lentiviruses protects motor function in SOD1 G93A ALS mice. The mice were injected with saline, lentiviruses containing GFP or a mixture of three types of lentiviruses each containing one of the three genes; EAAT2, NRF2 or GDH2 (MIX). Male (A) and female (B) motor function deterioration during disease progression as determined by Rotarod (for MIX, P<0.001 as determined by two way ANOVA for repeated measures. 12<n>17 animals per group per gender).
Figure 9B:
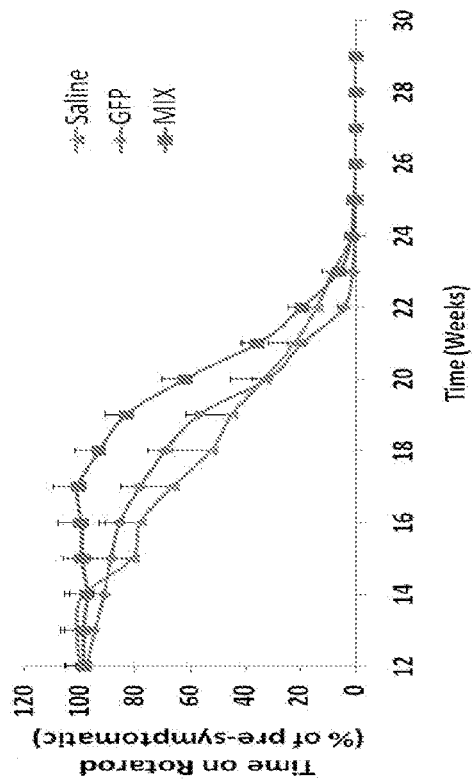

The effect of the treatment on motor performance was evaluated by Rotarod measurement. The treatment significantly slowed down the deterioration of motor function. Mice treated with saline or GFP reached 65% of their pre-symptomatic motor capabilities at the age of 17 to 18 weeks in males respectively and 19 weeks in both female groups. The treatment was able to significantly delay this loss in both male and female mice reaching the 65% mark at the ages of 20 and 22 weeks respectively (FIG. 9).

Figure 10A:
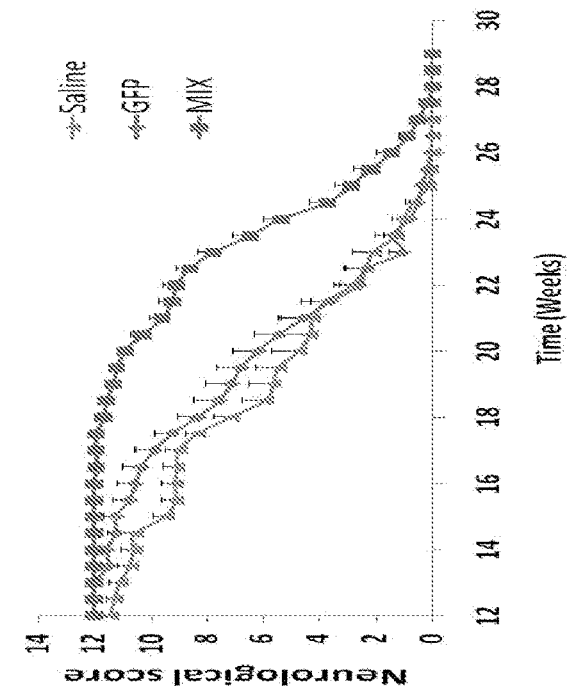
FIGS. 10A-B are graphs illustrating that treatment with EAAT2, NRF2 and GDH2 containing lentiviruses preserves neurological score in SOD1 G93A ALS mice. The mice were injected with saline, lentiviruses containing GFP or a mixture of three types of lentiviruses each containing one of the three genes; EAAT2, NRF2 or GDH2 (MIX). Male (A) and female (B) neurological score deterioration during disease progression (for MIX, P<0.001 as determined by two-way ANOVA for repeated measures. 12<n>17 animals per group per gender).
Figure 10B:
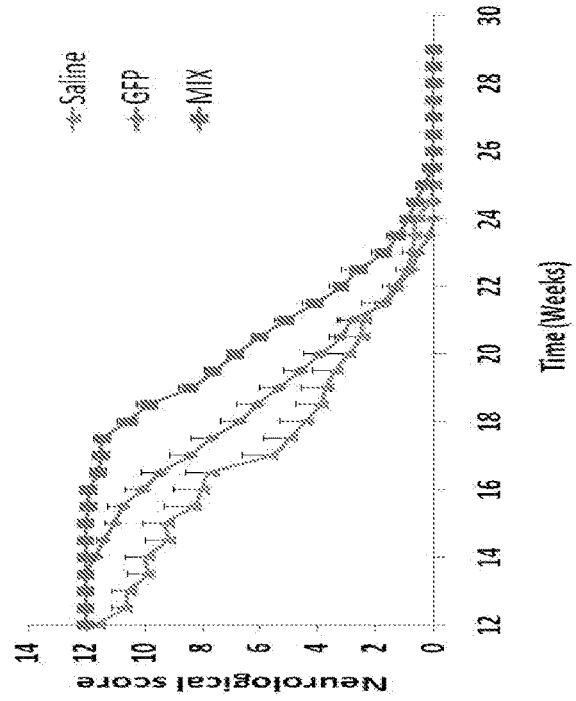

The parameters evaluated up until this point are rather rigid parameters. A more refined parameter of the disease progression was also evaluated. Use of such a parameter would allow observing the progression of the disease in a more sensitive way and observing more subtle changes. One such parameter is evaluation of mice neurological score using the ladder test. Unlike other parameters evaluated, the sensitivity of this test enabled to start observing symptomatic changes in the animals at the much earlier age. Mice treated with saline or GFP reached a neurological score of 8 indicating clear neurological deficits at the age of 16, 17.5 weeks in males and 17.5, 18 weeks in females respectively. The treatment was able to significantly delay this loss in both male and female mice reaching similar neurological deficits at the ages of 19 and 22.5 weeks respectively (FIG. 10).

In this ALS mouse model pre-clinical symptoms begin at an early age, whereas the onset of clinical symptoms occurs at a much later stage. The animals' quality of life was improved by delaying the onset of clinical symptoms. The onset of symptoms was defined as a 5% reduction in the animals' mass. In male mice symptoms were first observed at 131.69±5.24 and 133.46±5.24 days in mice treated with saline or GFP. However, symptom onset was significantly delayed in males treated with all three genes and began at the age of 144.92±2.88 days. In female mice the symptoms begin at a slightly older age, females treated with saline or GFP showed symptoms at 142.46±3.90 and 144.13±3.53 days respectively. The treatment significantly delayed the onset of symptoms with females treated with all three genes developing symptoms at 157.70±2.85 days (FIG. 11).

No safety concern or treatment-related adverse events were observed during the study.

One of the most important parameters in the evaluation of the potential clinical relevance of treatments for ALS is whether the treatment can increase the animals' life span. The treatment significantly prolonged survival in male mice by 18.96±4.81 and 12.5±2.40 days compared to mice treated with saline or GFP respectively (FIGS. 12A,B). This correlates with a 119.66% increased survival from the onset of symptoms in treated mice (compared to saline, FIG. 12C). In females, the survival was increased even further, with the treatment prolonging survival by 21.31±4.32 and 20.83±3.17 days compared to mice treated with saline or GFP respectively (FIGS. 12D,E). This correlates with a 136.27% increased survival from the onset of symptoms in treated mice (compared to saline, FIG. 12F).

Taken together these results show that the novel treatment strategy has a remarkable therapeutic potential in the SOD1 G93A mouse model of ALS.

Figure 13:
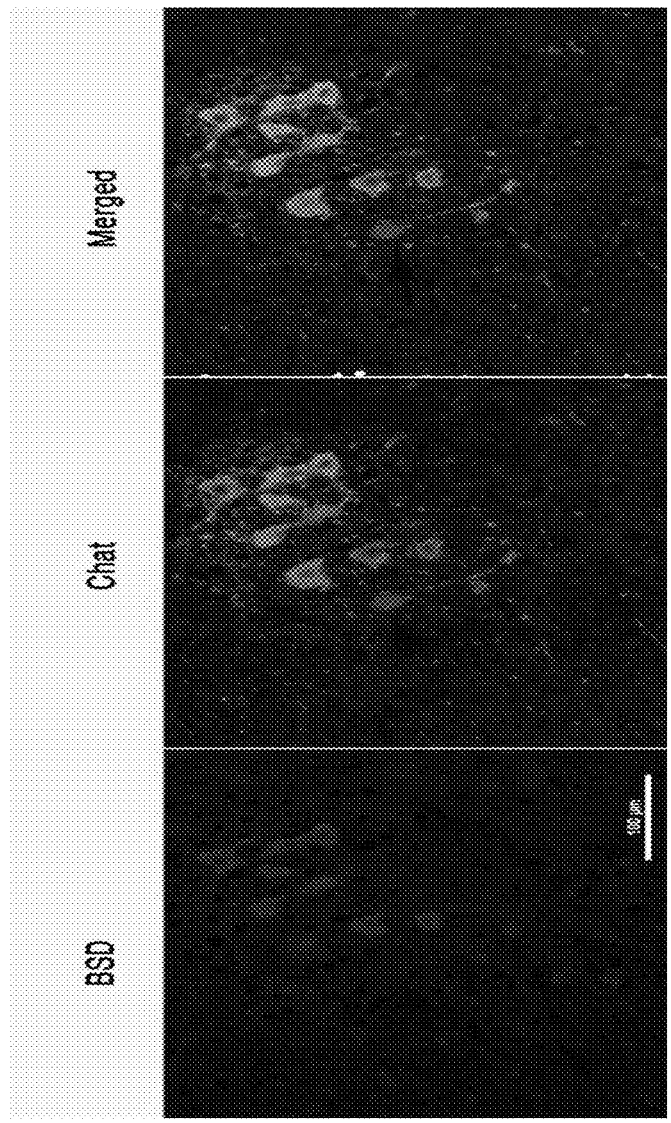
FIG. 13 illustrates that lentiviral vectors are expressed in the spinal cord cells. A representative image of a C5 spinal cord section of SOD1 G93A mice that were injected with lentiviral vectors. BSD was used as a resistance viral marker that indicates the expression of the viral vectors in the spinal cord cells (BSD positive, red). motor neurons (ChAT positive, green).

Expression of the Lentiviral Vectors in the Spinal Cord Cells: Mice were sacrificed 60 days following the treatment; immunohistochemistry was performed on spinal cord samples to evaluate the dispersion of the vectors into the spinal cord cells and expression of the viral marker for resistance-BSD (Blasticidin S Deaminase). The spinal cord samples were stained for BSD to detect viral protein expression and ChAT to detect motor neurons. As demonstrated in FIG. 13, the three lentiviral vectors disperse through the spinal cord cells and express their viral protein marker. It was also noted that the viral protein marker was also expressed in non motor neuron cell and was not expressed in all the detected motor neuron cells.

Figure 14:
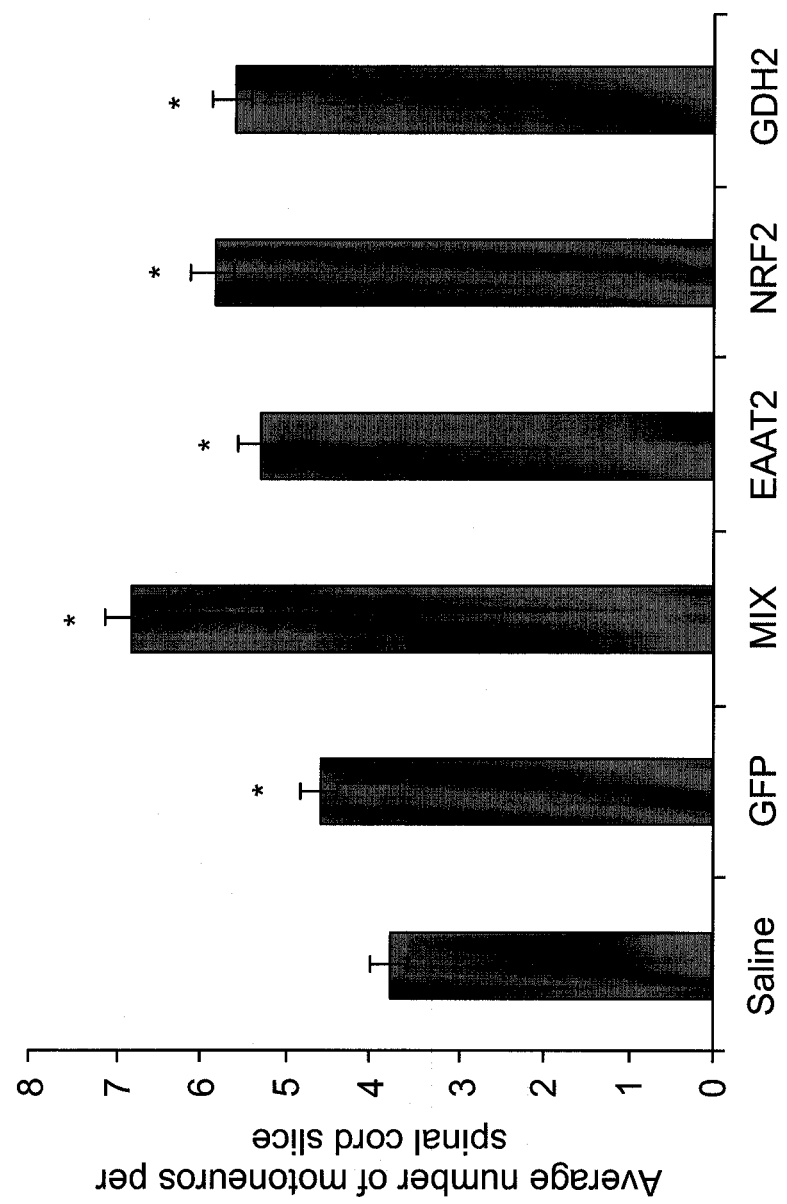
FIG. 14 is a bar graph illustrating that treatment with EAAT2, NRF2 and GDH2 preserves motoneuron viability The mice were injected with saline, lentiviruses containing GFP or a mixture of three types of lentiviruses each containing one of the three genes; EAAT2, NRF2 or GDH2 (MIX). (*P<0.001 as determined by ANOVA, n=4 animals and 12-14 spinal cord slices).

The spinal cord sections were also stained for ChAT and the number of motoneurons was counted (n=12-14 spinal cord sections). Treatment with LV-GFP slightly increased the motoneuron count compared to saline, treatment with each of the individual genes significantly increased the motoneuron count (neurons per slice), compared to saline and compared to GFP. While treatment with all three genes increased the motoneuron count even further (almost 2 fold increase as compared to Saline) than each of the individual genes (FIG. 14).

Summarizing, the results of the in vivo studies demonstrated that the combined treatment with EAAT2, NRF2 and GDH2 lentiviruses:

has a synergistic effect,
preserves body weight,
reduces the loss of hindlimb reflex,
protects motor function,
preserves neurological score,
delays the onset of symptoms,
increased survival.
no safety concerns were observed Example 4

Outline of a Clinical Trial Using EAAT2, NRF2 and GDH2 Lentivirus

Table 2 herein below outlines a proposed Phase 1/2 clinical study in patients with advanced rapidly progressive ALS as presented in the synopsis below:

TABLE 2

| | |
|---|---|
| Protocol Title: | A Phase 1/2 study to assess Safety and Efficacy of Intrathecal injection administration of EAAT2, NRF2 and GDH2 lentivirus for the treatment of advanced rapidly progressive ALS |
| Phase: | Phase 1/2 |
| Study Center(s): | TBD |
| Objectives: | The primary objectives of this study are: 1. to evaluate the safety and tolerability of EAAT2, NRF2 and GDH2 lentivirus for the treatment of advanced rapidly progressive ALS The secondary objectives of this study are: 1. to evaluate the efficacy of EAAT2, NRF2 and GDH2 lentivirus for the treatment of advanced rapidly progressive ALS 2. To characterize the PK & PD profile and immune responses of EAAT2, NRF2 and GDH2 lentivirus. |
| Study Design: | A Phase 1/2 study comprised of two dosages. Eligible subjects, defined as patients with advanced rapidly progressive ALS, will be enrolled in the study to one of the two cohorts. Eligible patients 'will undergo testing in the week prior to delivery of EAAT2, NRF2 and GDH2 lentivirus: body weight, BMI, Physical examination, Vital signs, ALSFRS-R (ALS Functional Rating Scale - Revised)Score, Neurological Examination, FVC (Forced Vital Capacity), Muscle Bulk (MVIC—Maximal Voluntary Isometric Contraction), Muscle Circumference, EMG (Electromyography), blood count, biochemistry, Coagulation and Urinalysis. Single intrathecal injection of EAAT2, NRF2 and GDH2 lentivirus will be administered. In the absence of signs of toxicity and under appropriate medical surveillance, the administered dose will be increased in new patients. Planned doses: $50 \times 10^8$ infectious viral particles, $1 \times 10^9$ infectious viral particles. The patients will be assessed on a bi-monthly or monthly basis with a follow up of 6 months according to the table below: |

TABLE 2-continued

|  | Assessment Parameters | Monthly | Bi-Monthly |
|---|---|---|---|
|  | Body Weight | ✓ |  |
|  | BMI | ✓ |  |
|  | Physical Examination | ✓ |  |
|  | Vital Signs | ✓ |  |
|  | ALSFRS-R Score | ✓ |  |
|  | Neurological Examination | ✓ |  |
|  | FVC | ✓ |  |
|  | Muscle Bulk (MVIC) | ✓ |  |
|  | Muscle Circumference | ✓ |  |
|  | Concomitant Drugs | ✓ |  |
|  | EMG |  | ✓ |
|  | Hematology CBC |  | ✓ |
|  | Blood Biochemistry |  | ✓ |
|  | Coagulation Tests |  | ✓ |
|  | Urinalysis |  | ✓ |
|  | Blood samples for immune response evaluation will be collected 2 weeks following the administration and monthly thereafter for 6 months. |  |  |
|  | Blood and cerebrospinal fluid samples for PK & PD will be collected following the administration of NeuRevive. |  |  |
|  | Following the 6 month follow up, Patients will be monitored yearly for 15 years for delayed adverse events. |  |  |
| Drug Name/Dosage: | 12 patients will be enrolled into 2 cohorts. Two successive dosages will be administered by Intrathecal injections beginning at $1 \times 10^8$ infectious viral particle, to be increased to $1 \times 10^9$ infectious viral particles. Dose escalation will only be authorized in the absence of toxicity for the previous dose. |  |  |
| Patient Population: | A Phase 1/2 study for eligible patients with advanced rapidly progressive ALS |  |  |
| Inclusion Criteria: | Male or female patients who meet all of the following criteria are eligible for this study.<br>1. Consenting patients fulfilling the El Escorial criteria for definite ALS (sporadic and not familial)<br>2. Age: 20-75, males and (non-pregnant) females<br>3. The patients are mentally intact and psychologically stable<br>4. Patients are at a progressive stage of the disease with an ALS-FRS scale of 6-30 and after loss of at least 12 ALSFRS points in the last 12 months<br>5. Patient with at least 60% FVC<br>6. Participant understands the nature of the procedure and provides written informed consent prior to any study procedure. |  |  |
| Exclusion Criteria: | Patients who meet any of the following criteria are not eligible for this study.<br>1. Concurrent therapy that, in the Investigator's opinion, would interfere with the evaluation of the safety or efficacy of the study medication.<br>2. Treatment with any investigational product within the last 12 months, or enrollment in any active study involving the use of investigational devices or drugs.<br>3. Presence of any other condition or circumstance that, in the judgment of the Investigator, might increase the risk to the patient or decrease the chance of obtaining satisfactory data to achieve the objectives of the study.<br>4. Presence of HBV, HCV or HIV.<br>5. Patients suffering from significant cardiac, renal or hepatic failure or any other disease that may endanger the patient or interfere with the ability to interpret the results<br>6. Patients with active infections<br>7. Patient has high protein in the CSF (Protein >50 mg/ml)<br>8. Patient has lymphocytosis in the CSF (lymphocytes >5/ml).<br>9. Patient is positive for anti-GM1 antibodies.<br>10. Patient has significant conduction blocks or slow nerve conduction velocities (a reduction of more than 30%) confirmed by nerve conduction velocity - EMG studies.<br>11. The patient is a respiratory dependent patient.<br>12. Patients with renal failure (Cr >2 mg/dl).<br>13. Patients with impaired hepatic function (ALT, AST or GGT 2-fold higher than normal upper limit). |  |  |

TABLE 2-continued

| | |
|---|---|
| Primary Endpoint: | Monitoring of adverse events, |
| Safety Parameters: | Physical examinations,<br>Vital Signs (HR, BP, RR, Body temperature),<br>Concomitant medications<br>Clinical laboratory parameters:<br>Hematology, Biochemistry, coagulation<br>Urinalysis<br>immune responses |
| Secondary Endpoints:<br>Efficacy parameters: | preliminary efficacy assessment will be based on<br>observation of the following variables along the study post-<br>treatment follow up period: ALS-FRS-R, neurological<br>Examination, muscle strength grading (MVIC) by muscle<br>chart, forced vital capacity (FVC), upper and lower<br>extremities circumference (cm), EMG parameters, need<br>and time to tracheotomy or permanent assisted ventilation<br>and overall survival. |
| Cont-Secondary<br>Endpoints: | Pharmacokinetics and Pharmacodynamics: Analysis of the<br>vector delivery into the target tissue, persistence of<br>expression and the presence of the functional proteins<br>will be evaluated using quantitative PCR,<br>immunocytochemistry and measurement of total and<br>specific proteins activities in subsets of patients who<br>consented for the muscle and cerebrospinal fluid biopsy.<br>Immunogenicity: blood samples collection to evaluate<br>immune reactions against the vector, trangenes,<br>endogenous proteins |
| Statistical Methods: | The analyses and statistical methods will be descriptive<br>in nature and will be designed to detect the trend of<br>study outcomes. The study will be Exploratory Non Powered. |

Example 4

Therapeutic Effect of Gene Therapy with EAAT2, NRF2 and GDH2 in a Mouse Model of Multiple System Atrophy (MSA)

MSA is characterized by abnormal accumulation of α-synuclein mainly in oligodendrocytes. To counteract the abnormalities observed in MSA, the present inventors injected mice with a mixture of three genes, (encoding EAAT2, NRF2 and GDH2) via a lenti-viral construct.

Figure 15:
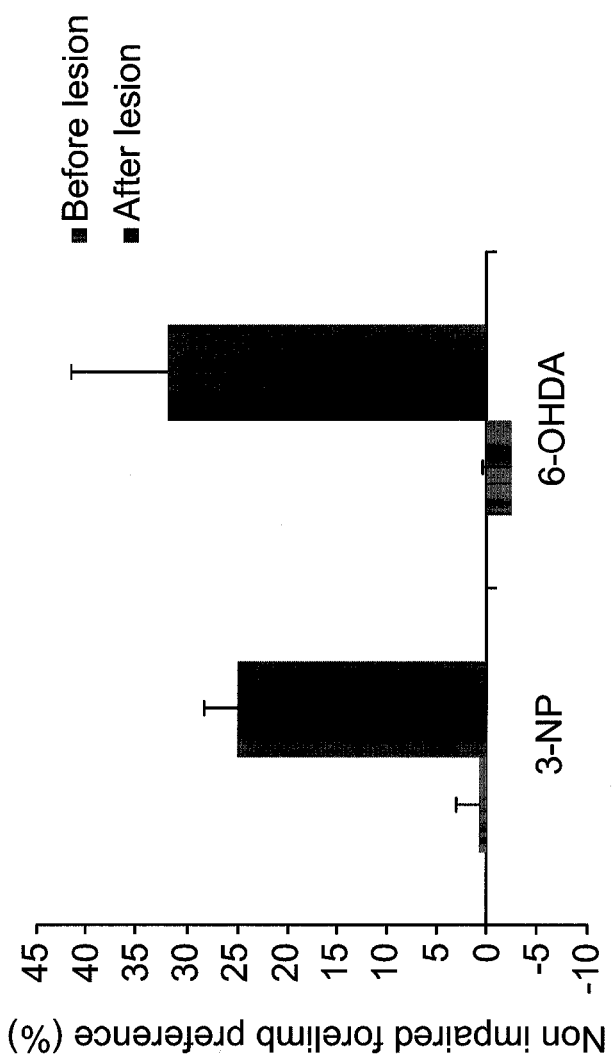
FIG. 15 is a graph illustrating the effect of 3-NP administration on motor activity.

Mouse Model: The striatal and nigral degeneration found in MSA-P can be reproduced using 3-Nitropropionic acid (3-NP), a mitochondrial complex II inhibitor, by administrating it into the striatum of rodents to create a model of MSA. As illustrated in FIG. 15, motor deficiency is severely hampered in the 3-NP mouse, as measured by the cylinder test. As illustrated in FIGS. 16A-B, differential rotation behavior is severely effected following 3-NP or 6-OHDA treatment in mice. Following amphetamine administration, there was a high number of ipsilateral rotations indicating neurodegeneration of dopaminergic cell (FIG. 16A). Following apomorphine administration, there was a high number of ipsilateral rotations indicating neurodegeneration of cells with dopamine receptors (FIG. 16B). Contralateral rotations after apomorphine treatment indicates overexpression of dopamine receptors.

Experimental Set-Up: At −2 weeks, the lentivirus was administered to the right striatum of the mice. At 0 weeks, 3-NP was administered. Drug induced rotation cylinder test was effected at +2 and +4 weeks.

Results

As illustrated in FIG. 17, apomorphine-induced rotational behavior was reduced following administration of each of the lentiviruses with the highest effect noted on administration of a mixture of each of the lentiviruses.

Figure 18:
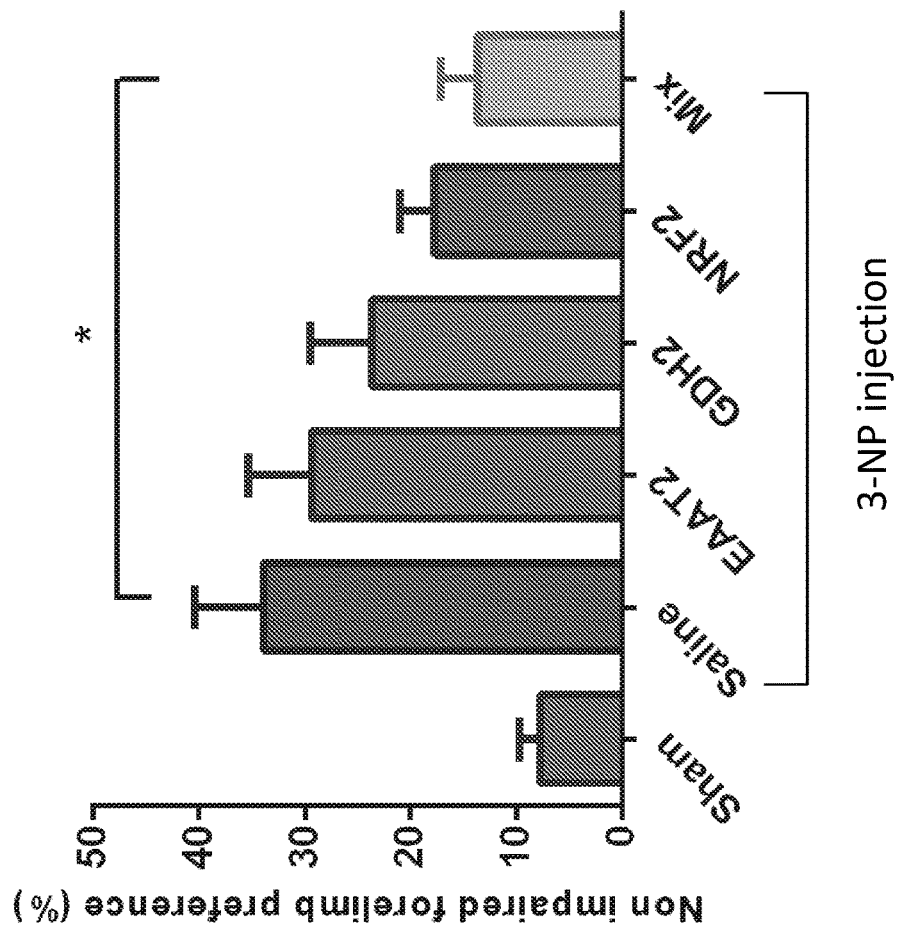
FIG. 18 is a graph illustrating the effect of mice treated with EAAT2, NRF2 and GDH2 (MIX) on motor function (Cylinder test) following 3-NP administration.

As illustrated in FIG. 18, motor function was improved following administration of each of the lentiviruses with the highest effect noted on administration of a mixture of each of the lentiviruses.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Attwell D. 2000. Brain uptake of glutamate: food for thought. J Nutr. 130(4S Sup p1):1023S-5S.

Beers D R, Henkel J S, Xiao Q, Zhao W, Wang J, Yen A A, Siklos L, McKercher S R, Appel S H. 2006. Wild-type microglia extend survival in PU.1 knockout mice with familial amyotrophic lateral sclerosis. *Proc Natl Acad Sci USA*. 103:16021-6.

Bendotti C, Tortarolo M, Suchak S, Calvaresi N, Carvelli L, Bastone A, Rizzi M, Rattray M, Mennini T. 2001. Transgenic SOD1 G93A mice develop reduced GLT-1 in spinal cord without alterations in cerebrospinal fluid glutamate levels. J Neurochem 79:737-746.

Benkler C, Offen D, Melamed E, Kupershmidt L, Amit T, Mandel S, Youdim M B H, Weinreb O. 2010. Recent advances in amyotrophic lateral sclerosis research: Perspectives for personalized clinical application. EPMA 1:343-361.

Boillée S, Vande Velde C, Cleveland D W. 2006. ALS: a disease of motor neurons and their nonneuronal neighbors. *Neuron.* 52:39-59.

Bogaert E, d'Ydewalle C, Van Den Bosch L. 2010. Amyotrophic lateral sclerosis and excitotoxicity: from pathological mechanism to therapeutic target. *CNS Neural Disord Drug Targets.* 9(3):297-304.

Brown D R. 2000. Neuronal release of vasoactive intestinal peptide is important to astrocytic protection of neurons from glutamate toxicity. *Mol Cell Neurosci.* 15(5):465-75.

Calkins M J, Vargas M R, Johnson D A, Johnson J A. 2010. Astrocyte-specific overexpression of Nrf2 protects striatal neurons from mitochondrial complex II inhibition. *Toxicol Sci.* 115(2):557-68.

Cashman N, Durham H, Blusztajn J, Oda K, Tabira T, Shaw I, Dahrouge S, Antel J P. 1992. Neuroblastoma×spinal cord (NSC) hybrid cell lines resemble developing motor neurons. Dev Dyn 194:209-221.

Charles T, Swash M. 2001. Amyotrophic lateral sclerosis: current understanding. *J Neurosci Nurs.* 33:245-53.

Clement A M, Nguyen M D, Roberts E A, Garcia M L, Boillee S, Rule M, McMahon A P, Doucette W, Siwek D, Ferrante R J, Brown R H Jr, Julien J P, Goldstein L S, Cleveland D W. 2003. Wild-type nonneuronal cells extend survival of SOD1 mutant motor neurons in ALS mice. *Science.* 302:113-7.

Cozzolino M, Ferri A, Carri M T. 2008. Amyotrophic lateral sclerosis: from current developments in the laboratory to clinical implications. Antioxid Redox Signal. 10(3):405-43.

Danbolt N C. 2001. Glutamate uptake. *Prog Neurobiol.* 65(1):1-105. de Hemptinne I, Vermeiren C, Maloteaux J M, Hermans E. 2004. Induction of glial glutamate transporters in adult mesenchymal stem cells. J Neurochem. 91(1):155-66.

Di Giorgio F P, Carrasco M A, Siao M C, Maniatis T, Eggan K. 2007. Non-cell autonomous effect of glia on motor neurons in an embryonic stem cell-based ALS model. *Nat Neurosci.* 10:608-11.

Eggett C, Crosier S, Manning P, Cookson M, Menzies F, McNeil C, Shaw P J. 2000. Development and characterisation of a glutamatesensitive motor neurone cell line. J Neurochem 74:1895-1902.

Foran E, Trotti D. 2009. Glutamate transporters and the excitotoxic path to motor neuron degeneration in amyotrophic lateral sclerosis. *Antioxid Redox Signal.* 11(7): 1587-602.

Fu H, Kang L, Jennings J S, Moy S S, Perez A, Dirosario J, McCarty D M, Muenzer J. 2007. Significantly increased lifespan and improved behavioral performances by rAAV gene delivery in adult mucopolysaccharidosis IIIB mice. *Gene Ther.* 14(14):1065-77.

Fu H, Muenzer J, Samulski R J, Breese G, Sifford J, Zeng X, McCarty D M. 2003. Self-complementary adeno-associated virus serotype 2 vector: global distribution and broad dispersion of AAV-mediated transgene expression in mouse brain. *Mol Ther.* 8(6):911-7.

Hybertson B M, Gao B, Bose S K, McCord J M. 2011. Oxidative stress in health and disease: the therapeutic potential of Nrf2 activation. Mol Aspects Med. 32(4-6): 234-46.

Ilieva H, Polymenidou M, Cleveland D. 2009. Non-cell autonomous toxicity in neurodegenerative disorders: ALS and beyond. *J Cell Biol.* 187:761-72.

Kraft A D, Johnson D A, Johnson J A. 2004. Nuclear factor E2-related factor 2-dependent antioxidant response element activation by tert-butylhydroquinone and sulforaphane occurring preferentially in astrocytes conditions neurons against oxidative insult. *J Neurosci.* 24(5): 1101-12.

Lee Y, Park H W, Park S G, Cho S, Myung P K, Park B C, Lee do H. 2007. Proteomic analysis of glutamate-induced toxicity in HT22 cells. *Proteomics.* 7(2):185-93.

Lev N, Ickowicz D, Barhum Y, Melamed E, Offen D. 2009. DJ-1 changes in G93A-SOD1 transgenic mice: implications for oxidative stress in ALS. J Mol Neurosci. 38(2): 94-102.

Louboutin J P, Reyes B A, Agrawal L, Van Bockstaele E J, Strayer D S. 2012. Intracisternal rSV40 administration provides effective pan-CNS transgene expression. *Gene Ther.* 19(1):114-8.

Lynch D R, Guttmann R P. 2002. Excitotoxicity: perspectives based on N-methyl-D-aspartate receptor subtypes. *J Pharmacol Exp Ther.* 300(3): 717-23.

Mattson M P. Glutamate and neurotrophic factors in neuronal plasticity and disease. Ann N Y Acad Sci. 2008 November; 1144:97-112.

Matusica D, Fenech M, Rogers M, Rush R. 2008. Characterization and use of the NSC-34 cell line for study of neurotrophin receptor trafficking. J Neurosci Res 86:553-565.

Maragakis N J, Rothstein J D. 2001. Glutamate transporters in neurologic disease. *Arch Neurol.* 58(3):365-70.

Molz S, Decker H, Dal-Cim T, Cremonez C, Cordova F M, Leal R B, Tasca C I. 2008. Glutamate-induced toxicity in hippocampal slices involves apoptotic features and p38 MAPK signaling. *Neurochem Res.* 33(1):27-36.

Offen D, Barhum Y, Melamed E, Embacher N, Schindler C, Ransmayr G. 2009. Spinal cord mRNA profile in patients with ALS: comparison with transgenic mice expressing the human SOD-1 mutant. J Mol Neurosci. 38(2):85-93.

Oliveira A, Pereira R. 2009. Amyotrophic lateral sclerosis (ALS): three letters that change the people's life. For ever. *Arq Neuropsiquiatr.* 67:750-82.

Rothstein J. 2009. Current hypotheses for the underlying biology of amyotrophic lateral sclerosis. Ann Neurol. 65 Suppl 1:S3-9.

Rothstein J, Martin L, Kuncl R. 1992. Decreased glutamate transport by the brain and spinal cord in amyotrophic lateral sclerosis. N Engl J Med 22:1464-1468.

Rothstein J, Patel S, Regan M R, Haenggeli C, Huang Y H, Bergles D E, Jin L, Dykes Hoberg M, Vidensky S, Chung D S, Toan S V, Bruijn L I, Su Z Z, Gupta P, Fisher P B. 2005. Beta-lactam antibiotics offer neuroprotection by increasing glutamatetransporter expression. Nature. 6; 433(7021):73-7.

Rothstein J, Van Kammen M, Levey A, Martin L, Kuncl R. 1995. Selective loss of glial glutamate transporter GLT-1 in amyotrophic lateral sclerosis. Ann Neurol 38:73-84.

Rothstein J, Dykes-Hoberg M, Pardo C, Bristol L, Jin L, Kuncl R, Kanai Y, Hediger M A, Wang Y, Schielke J P, Welty D F. 1996. Knockout of glutamate transporters reveals a major role for astroglial transport in excitotoxicity and clearance of glutamate. Neuron 16:675-686.

Sheldon A L and Robinson M B. 2007. The role of glutamate transporters in neurodegenerative diseases and potential opportunities for intervention. Neurochem Int. 51(6-7): 333-55.

Shih A Y, Johnson D A, Wong G, Kraft A D, Jiang L, Erb H, Johnson J A, Murphy T H. 2003. Coordinate regulation of glutathione biosynthesis and release by Nrf2-expressing glia potently protects neurons from oxidative stress. *J Neurosci.* 23(8):3394-406.

Staats K, Van Den Bosch L. 2009. Astrocytes in amyotrophic lateral sclerosis: direct effects on motor neuron survival. *J Biol Phys.* 35:337-46.

Sonnewald U, Qu H, Aschner M. 2002. Pharmacology and toxicology of astrocyte-neuron glutamate transport and cycling. J Pharmacol Exp Ther. 301(1):1-6.

Valdmanis P, Daoud H, Dion P, Rouleau G. 2009. Recent advances in the genetics of amyotrophic lateral sclerosis. *Curr Neurol Neurosci Rep.* 9:198-205.

Van Damme P, Dewil M, Robberecht W, Van Den Bosch L. 2005. Excitotoxicity and amyotrophic lateral sclerosis. *Neurodegener Dis.* 2(3-4):147-59.

Van Den Bosch L, Robberecht W. 2008. Crosstalk between astrocytes and motor neurons: what is the message? *Exp Neurol.* 211:1-6.

Vargas M R, Johnson J A. 2009. The Nrf2-ARE cytoprotective pathway in astrocytes. *Expert Rev Mol Med.* 3; 11:e17.

Vargas M R, Johnson D A, Sirkis D W, Messing A, Johnson J A. 2008. Nrf2 activation in astrocytes protects against neurodegeneration in mouse models of familial amyotrophic lateral sclerosis. *J Neurosci.* 28(50):13574-81.

Vargas M R, Pehar M, Cassina P, Beckman J S, Barbeito L. 2006. Increased glutathione biosynthesis by Nrf2 activation in astrocytes prevents p75NTR-dependent motor neuron apoptosis. *J Neurochem.* 97(3):687-96.

Weishaupt J, Bartels C, Pölking E, Dietrich J, Rohde G, Poeggeler B, Mertens N, Sperling S, Bohn M, Hüther G, Schneider A, Bach A, Sirén A L, Hardeland R, Bähr M, Nave K A, Ehrenreich H. 2006. Reduced oxidative damage in ALS by high-dose enteral melatonin treatment. J Pineal Res 41:313-323.

Wijesekera L, Leigh P N. 2009. Amyotrophic lateral sclerosis. *Orphanet J Rare Dis.* 3:4:3.

Xiao S, McLean J, Robertson J. 2006. Neuronal intermediate filaments and ALS: a new look at an old question. Biochim Biophys Acta. 1762(11-12):1001-12.

Yamanaka K, Chun S J, Boillee S, Fujimori-Tonou N, Yamashita H, Gutmann D H, Takahashi R, Misawa H, Cleveland D W. 2008. Astrocytes as determinants of disease progression in inherited amyotrophic lateral sclerosis. *Nat Neurosci.* 11:251-3.

---

What is claimed is:

1. A method of treating a disease selected from the group consisting of ischemic injury, cerebral ischemia, and a neurodegenerative disorder selected from the group consisting of amyotrophic lateral sclerosis, and multiple system atrophy, in a subject in need thereof comprising administering to the subject a therapeutically effective amount of a combination of three agents, wherein a first of said three agents is a polynucleotide encoding Nuclear factor (erythroid-derived 2)-like 2 (Nrf2), a second of said three agents is a polynucleotide encoding a glutamate transporter and a third of said three agents is a polynucleotide encoding a glutamate dehydrogenase, thereby treating the disease, and wherein the glutamate transporter is excitatory amino acid transporter (EAAT) 2 (EAAT2) and the glutamate dehydrogenase is glutamate dehydrogenase 2 (GDH2).

2. The method of claim 1, wherein the neurodegenerative disorder is amyotrophic lateral sclerosis or multiple system atrophy.

3. The method of claim 1, further comprising administering an antioxidant.

4. The method of claim 3, wherein said antioxidant comprises an agent selected from the group consisting of Coenzyme Q10, thiol, ascorbic acid, polyphenol, glutathione, vitamin C, vitamin E, catalase, superoxide dismutase and peroxidase.

5. The method of claim 1, wherein said administering is effected via intra-cisternal (I.C.) administration or intra-muscular (I.M.) administration.

6. The method of claim 1, wherein said disease is ischemic injury or cerebral ischemia.

* * * * *

UNITED STATES PATENT AND TRADEMARK OFFICE
CERTIFICATE OF CORRECTION

PATENT NO. : 10,220,077 B2
APPLICATION NO. : 14/442731
DATED : March 5, 2019
INVENTOR(S) : Chen Benkler It is certified that error appears in the above-identified patent and that said Letters Patent is hereby corrected as shown below:

On the Title Page

Change the Assignee name from "RAMOT AT TEL-AVIV UNIVERSITY LTD." to
--Daniel Offen--.

Signed and Sealed this
Twenty-sixth Day of November, 2019

Andrei Iancu
*Director of the United States Patent and Trademark Office*